US008034914B2

(12) United States Patent
Hochberg

(10) Patent No.: US 8,034,914 B2
(45) Date of Patent: Oct. 11, 2011

(54) NUCLEIC ACID CONSTRUCTS, PHARMACEUTICAL COMPOSITIONS AND METHODS OF USING SAME FOR TREATING CANCER

(75) Inventor: Avraham Hochberg, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 315 days.

(21) Appl. No.: 12/067,410

(22) PCT Filed: Sep. 21, 2006

(86) PCT No.: PCT/IL2006/001110
§ 371 (c)(1),
(2), (4) Date: Aug. 5, 2008

(87) PCT Pub. No.: WO2007/034487
PCT Pub. Date: Mar. 29, 2007

(65) Prior Publication Data
US 2009/0221681 A1 Sep. 3, 2009

Related U.S. Application Data

(60) Provisional application No. 60/719,178, filed on Sep. 22, 2005.

(51) Int. Cl.
*C07H 21/04* (2006.01)
*C07H 21/02* (2006.01)
(52) U.S. Cl. ...................... 536/23.2; 536/23.1; 536/24.1; 536/24.2; 536/23.4
(58) Field of Classification Search .................. 536/23.2
See application file for complete search history.

(56) References Cited

U.S. PATENT DOCUMENTS

| | | | |
|---|---|---|---|
| 3,791,932 A | 2/1974 | Schuurs et al. | 195/103.5 R |
| 3,839,153 A | 10/1974 | Schuurs et al. | 195/103.5 R |
| 3,850,578 A | 11/1974 | McConnell | 23/230 B |
| 3,850,752 A | 11/1974 | Schuurs et al. | 195/103.5 R |
| 3,853,987 A | 12/1974 | Dreyer | 424/1 |
| 3,867,517 A | 2/1975 | Ling | 424/1 |
| 3,879,262 A | 4/1975 | Schuurs et al. | 195/63 |
| 3,901,654 A | 8/1975 | Gross | 23/230 B |
| 3,935,074 A | 1/1976 | Rubenstein et al. | 195/103.5 R |
| 3,984,533 A | 10/1976 | Uzgiris | 424/12 |
| 3,996,345 A | 12/1976 | Ullman et al. | 424/12 |
| 4,034,074 A | 7/1977 | Miles | 424/1 |
| 4,098,876 A | 7/1978 | Piasio et al. | 424/1 |
| 4,666,828 A | 5/1987 | Gusella | 435/6 |
| 4,683,202 A | 7/1987 | Mullis | 435/91 |
| 4,801,531 A | 1/1989 | Frossard | 435/6 |
| 4,879,219 A | 11/1989 | Wands et al. | 435/7 |
| 5,011,771 A | 4/1991 | Bellet et al. | 435/7.94 |
| 5,192,659 A | 3/1993 | Simons | 435/6 |
| 5,272,057 A | 12/1993 | Smulson et al. | 435/6 |
| 5,281,521 A | 1/1994 | Trojanowski et al. | 435/7.5 |
| 5,464,764 A | 11/1995 | Capecchi et al. | 435/172.3 |
| 5,487,992 A | 1/1996 | Capecchi et al. | 435/172.3 |
| 5,648,478 A | 7/1997 | Henderson | 536/241 |
| 5,955,273 A | 9/1999 | Hochberg et al. | 435/6 |
| 6,306,833 B1 | 10/2001 | Hochberg et al. | 514/44 |

FOREIGN PATENT DOCUMENTS

| | | |
|---|---|---|
| WO | WO9524503 | 9/1995 |
| WO | WO9918195 | 4/1999 |
| WO | WO2004024957 | 3/2004 |

OTHER PUBLICATIONS

Hennecke, 2001, Nucl Acids Res, 29:3327-3334.*
Schmidt-Wolf, 1996, Ann Hematol, 73:207-218.*
Perez, 1990, Cell, 63:251-258.*
Adriaenssens, E., et al. (2002) Exp Cell Res 275, 215-229.
Aigner, (2006) J. Biotechnol. 254, 12-25.
Ariel, I.., et al. (1994) Gynecol Oncol 53, 212-219.
Ariel, I., et al. (2004) Mol Carcinog 41, 69-76.
Ayesh, B., e al. (2003) Mol. Ther. 7, 535-541.
Ayesh, S., et al. (2002) Mol Carcinog 35, 63-74.
Bartolomei, M.S., et al. (1991) Nature 351, 153-155.
Bennet, M.J., et al. (1994) Protein Science 3, 1444-1463.
Brannan, C.I., (1990) Mol. Cell boil. 10, 28-36.
Bruns, C.J., et al. (1999) Neoplasia 1(1), 50-62.
Christopher and Wong, (2006) Curr. Pharm. Des. 1995-2006.
Corazza et al.,Gastroenterology, (2004) 127(3), 816-25.
Elkin, M., et al., (1995) FEBS Lett. 374, 57-61.
Elkin, M., et al. (1998) Carcinogenesis 19, 2095-2099.
Folkman, J., and Kalluri, R., (2004) Nature 427, 787.
Gilboa et al. (1986) Biotechniques 4 (6), 504-512.
Glazier et al., (1995) J. Urol. 154, 66-68.
Graveel, C.R., et al. (2001) Oncogene 20, 2704-2712.
Horiguchi, Y., Larchian, W.A., et al. (2000) Gene Ther. 7, 844-851.
Kaplan, R., et al. (2003) Cancer Res 63, 1475-1482.
Kyung-Jin Kim, (2004) Protein Science 13, 1698-1703.
Leibovitch, M.P., et al. (1991) Biochem. Biophys. Res. Commun. 180, 1241-1250.
Liang, C.Y., et al. (2004) Arch Virol. 149, 51-60.
Lottin, S., et al. (2002) Carcinogesis 23, 1885-1895. Lottin, S., et al. (2002) Oncogene 21, 1625-1631.
Lungwitz (2005) Eur. J. Phar. Biopharm. 60(2):247-66.
Lustig-Yariv, O., et al. (1997) Oncogene 15, 169-177.
Matouk, I., et al. (2004) Biochem. Biophys. Res. Commun. 318, 916-919.
Matouk, I., et al. (2005) Cancer Therapy 3, 249-266.
Mizutani, Y., et al. (1994) Urol. Res. 22, 261-6.
Morimoto, H., et al. (1991) J. Immunol. 147, 2609-2616.
Morimoto, H., et al. (1992) J. Immunol. 149, 2089-94.
Niell, H.B., et al. (1994) Urol. Res. 22, 247-250.
Ohana, P., et al. (2004) Gene Ther. Mol. Biol 8, 181-192.
Raab, Gerhard et al. (1997) Biochimica et Biophysica Acta (BBA)/ Reviews on Cancer 1333, F179-F199.
Rachmilewitz, J., et al. (1992) FEBS Lett. 309, 25-28.
Rachmilewitz, J., et al. (1995) Oncogene 11, 863-870.

(Continued)

*Primary Examiner* — Valarie Bertoglio
(74) *Attorney, Agent, or Firm* — Winston & Strawn LLP

(57) ABSTRACT

A nucleic acid construct that includes (i) a first nucleic acid sequence encoding TNF alpha; (ii) a second nucleic acid sequence encoding a Diphtheria toxin; and (iii) at least one additional nucleic acid sequence of a cancer specific promoter. The TNF alpha and Diphtheria toxin encoding sequences are under an expression control of the cancer specific promoter. Also provided are construct systems and methods and uses of same.

8 Claims, 15 Drawing Sheets

OTHER PUBLICATIONS

Rodesch, F., et al. (1991) Obstet. Gynecol. 80, 283-285.
Rodriguez et al. (1998) The Prostate 34, 259-269.
Rotwein et al. (1986) J. Biol. Chem. 261, 4828-4832.
Stuhlmuller, B., et al. (2003) Am. J. Pathol. 163, 901-911.
Tonkinson et al. (1996) Cancer Investigation 14(1), 54-65.
Venables, J.P., (2004) Cancer Res. 64, 2647-2654.
Wolff (2005) Acta Myol. 24, 202-8.
Zdanovsky, A.G., et al. (2000) Research in Microbiology 151, 557-562.
Zhang, Y., and Tycko, B., (1992) Nat. Genet. 1, 40-44.

* cited by examiner

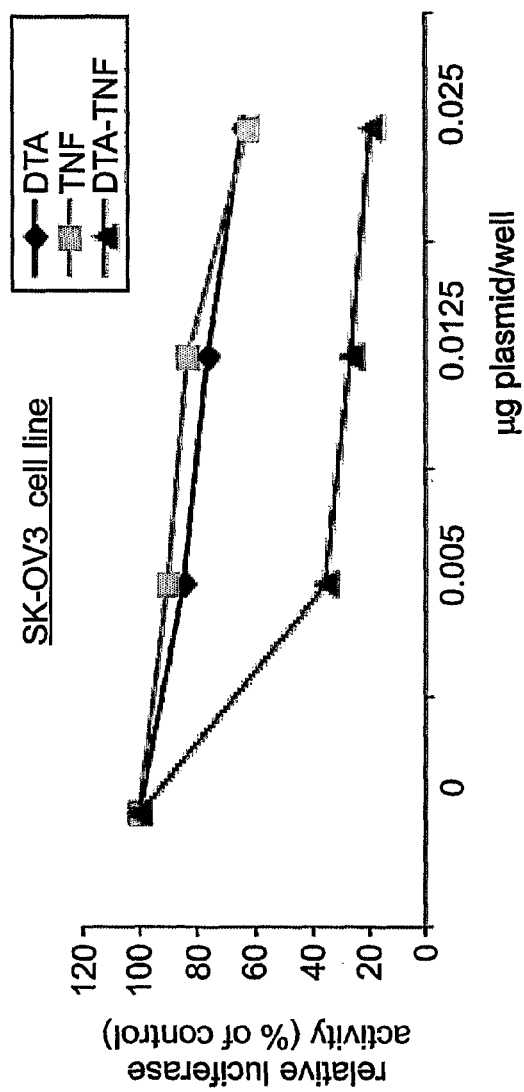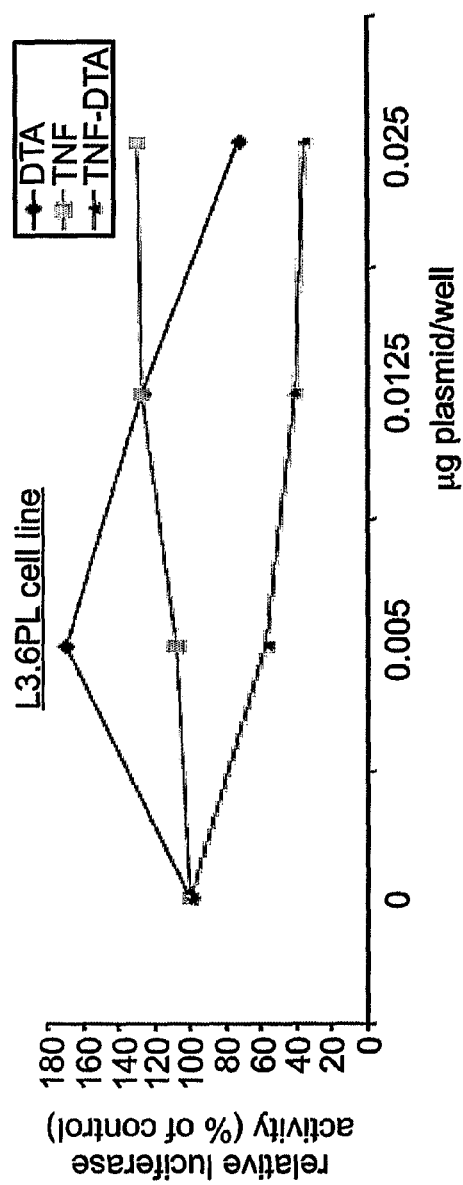
Fig. 5c
Fig. 5d

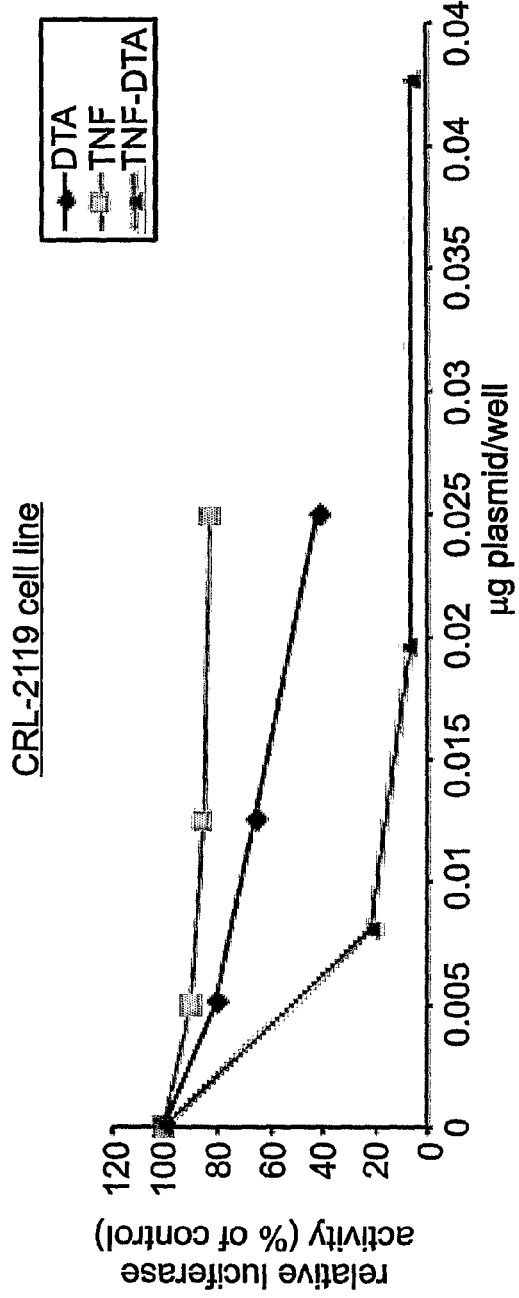
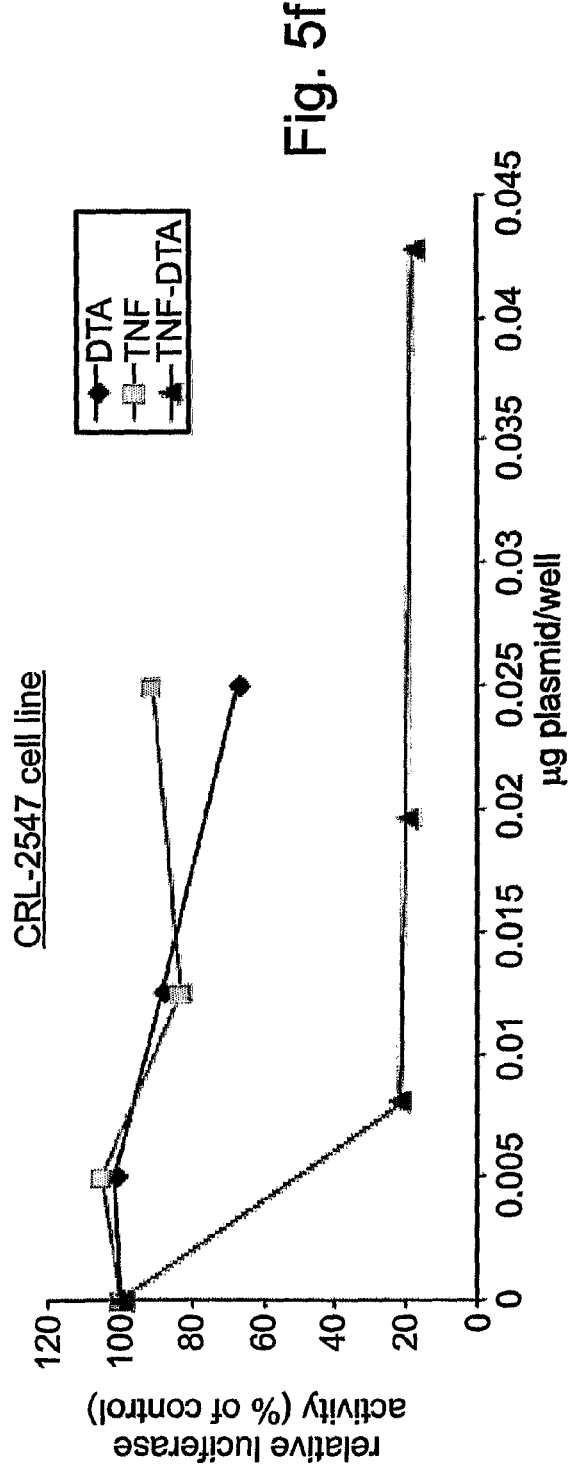

NUCLEIC ACID CONSTRUCTS, PHARMACEUTICAL COMPOSITIONS AND METHODS OF USING SAME FOR TREATING CANCER

This application is a 371 filing of International Patent Application PCT/IL2006/001110, filed Sep. 21, 2006, which claims the benefit of application No. 60/719,178 filed Sep. 22, 2005.

FIELD AND BACKGROUND OF THE INVENTION

The present invention relates to nucleic acid constructs, pharmaceutical compositions and methods of using such constructs for treating cancer.

Neoplasia is a process that occurs in cancer, by which the normal controlling mechanisms that regulate cell growth and differentiation are impaired, resulting in progressive growth. This impairment of control mechanisms allows a tumor to enlarge and occupy spaces in vital areas of the body. If the tumor invades surrounding tissue and is transported to distant sites (metastases) it will likely result in death of the individual.

The desired goal of cancer therapy is to kill cancer cells preferentially, without having a deleterious effect on normal cells. Several methods have been used in an attempt to reach this goal, including surgery, radiation therapy and chemotherapy.

Surgery was the first cancer treatment available, and still plays a major role in diagnosis, staging, and treatment of cancer, and may be the primary treatment for early cancers. However, although surgery may be an effective way to cure tumors confined to a particular site, these tumors may not be curable by resection due to micrometastatic disease outside the tumor field. Any cancer showing a level of metastasis effectively cannot be cured through surgery alone.

Radiation therapy is another local (nonsystemic) form of treatment used for the control of localized cancers. Many normal cells have a higher capacity for intercellular repair than neoplastic cells, rendering them less sensitive to radiation damage. Radiation therapy relies on this difference between neoplastic and normal cells in susceptibility to damage by radiation, and the ability of normal organs to continue to function well if they are only segmentally damaged. Thus, the success of radiation therapy depends upon the sensitivity of tissue surrounding the tumor to radiation therapy. Radiation therapy is associated with side effects that depend in part upon the site of administration, and include fatigue, local skin reactions, nausea and vomiting. In addition, radiation therapy is mutagenic, carcinogenic and teratogenic, and may place the patient at risk of developing secondary tumors.

Other types of local therapy have been explored, including local hyperthermia, photoradiation therapy and interstitial radiation. Unfortunately, these approaches have been met with only moderate success.

Local treatments, such as radiation therapy and surgery, offer a way of reducing the tumor mass in regions of the body that is accessible through surgical techniques or high doses of radiation therapy. However, more effective local therapies with fewer side effects are needed. Moreover, these treatments are not applicable to the destruction of widely disseminated or circulating tumor cells eventually found in most cancer patients. To combat the spread of tumor cells, systemic therapies are used.

One such systemic treatment is chemotherapy. Chemotherapy is the main treatment for disseminated, malignant cancers. However, chemotherapeutic agents are limited in their effectiveness for treating many cancer types, including many common solid tumors. This failure is in part due to the intrinsic or acquired drug resistance of many tumor cells. Another drawback to the use of chemotherapeutic agents is their severe side effects. These include bone marrow suppression, nausea, vomiting, hair loss, and ulcerations in the mouth. Clearly, new approaches are needed to enhance the efficiency with which a chemotherapeutic agent can kill malignant tumor cells, while at the same time avoiding systemic toxicity.

Because it is unlikely that gene transfer reaches every cell of a cancer, DNA based therapy approaches are thought to require the induction of a 'bystander' effect. An interesting and novel approach for this purpose is cytokine DNA based therapy. In particular, use of TNF-α seems an attractive strategy to prevent for example, bladder tumor recurrence after transurethral resection.

TNF-α is a multifunctional and immunoregulatory cytokine that exhibits direct tumor cell cytotoxicity, possesses anti-angiogenetic properties, and enhances antitumor immunity by activating immune cells such as dendritic cells and T cells. Induction of TNF-α is thought to be partly responsible for the effect of BCG immunotherapy in the prevention of TCC recurrences (1,2) and recombinant cytokine therapy has—in principle—proved efficacious for bladder cancer (3). However, systemic delivery of the TNF-alpha protein has had limited success clinically because of severe dose limiting toxic effects.

This limitation can be overcome by the use of a gene delivery approach, combined with a tumor specific promoter to express TNF-α in the tumor tissue, optionally together with a tumor specific expression of a toxin.

H19 was the first human imprinted non protein-coding gene to be identified showing expression of only the maternal allele (Rachmilewitz et al, 1992; Zhang and Tycko, 1992). It is also imprinted in mice (Bartolomei et al, 1991). H19 was mapped on the short arm of chromosome 11, band 15.5, homologous to a region of murine chromosome 7 (Leibovitch et al, 1991). It belongs to a group of genes that very likely does not code for a protein product (Brannan et al, 1990).

Studies of various tumors have demonstrated a re-expression or an over-expression of the H19 gene when compared to healthy tissues. Moreover in cancers of different etiologies and lineages, aberrant expression in allelic pattern was observed in some cases. While H19 shows mono-allelic expression in most tissues throughout development, with the exception of germ cells at certain stages of maturation, and in extra-villous trophoblasts, bi-allelic expression of this gene, referred as "relaxation of imprinting" or LOI, have been found in an increasing number of cancers, for example, hepatocellular carcinoma, liver neoplasms of albumin SV40 T antigen-transgenic rats, lung adenocarcinoma, esophageal, ovarian, rhabdomyosarcoma, cervical, bladder, head and neck squamous cell carcinoma, colorectal, uterus and in testicular germ cell tumors. Today nearly 30 types of cancers show dysregulated expression of H19 gene as compared to healthy tissues, with or without LOI. For recent review see (Matouk et al, 2005).

It was also shown that H19 over-expression of ectopic origin conferred a proliferative advantage for breast epithelial cells in a soft agar assay and in several combined immunodeficient (SCID) mice (Lottin et al, 2002). In tumors formed by the injection of cells of a choriocarcinoma-derived cell line (JEG-3), and a bladder carcinoma cell line (T24P), the $H_{19}$ level is very high when compared to the level of H19 in cells before injection (Rachmilewitz et al, 1995; Elkin et al, 1995; Lustig-Yariv et al, 1997).

Moreover, certain known carcinogens upregulate the expression of the H19 gene. A dramatic elevation of H19 RNA levels was detected in the airway epithelium of smokers without loss of imprinting (LOI) (Kaplan et al, 2003). BBN (N-butyl-N-(4-hydroxybutyl nitrosamine, a known carcinogen of the bladder) also induces the expression of H19 gene in the rat model of bladder cancer (Elkin et al, 1998; Ariel et al, 2004). Likewise, Diethylnitrosamine (a known carcinogen of the liver) induces the expression of H19 in a mice model of hepatocellular carcinoma (Graveel et al, 2001).

The specific expression of H19 gene in cancer cells has prompted its use in clinical applications for diagnosing cancer.

Thus, U.S. Pat. No. 5,955,273 to the present inventors teaches the use of H19 gene as a tumor specific marker.

PCT Pub. No. WO 9524503 teaches the detection of malignancies and their grading with a H19 gene probe by in-situ hybridization—useful for detecting presence/absence of malignancy in pediatric Wilms' Tumor.

PCT Pub. No. WO 04024957 teaches detecting cancer or the presence of residual cancer cells or micro-metastasis by detecting the presence of H119 RNA in the specimen.

The use of H19 promoter for specifically expressing cytotoxic agents in cancer cells has been suggested in PCT Pub. No. WO9918195 which teaches the specific expression of heterologous sequences, particularly genes encoding cytotoxic products, in tumor cells under the control of regulatory transcriptional sequences (e.g., H19 promoter).

To date cancer-specific gene therapy using TNFα and diphtheria toxin A under a cancer specific promoter has never been suggested or attempted.

SUMMARY OF THE INVENTION

According to one aspect of the present invention there is provided a nucleic acid construct comprising:
(i) a first nucleic acid sequence encoding TNF alpha;
(ii) a second nucleic acid sequence encoding a Diphtheria toxin; and
(iii) at least one additional nucleic acid sequence comprising a cancer specific promoter; the TNF alpha and Diphtheria toxin encoding sequences being under an expression control of the cancer specific promoter.

According to further features in preferred embodiments of the invention described below, the first nucleic acid sequence and the second nucleic acid sequence are transcriptionally linked via a linker nucleic acid sequence.

According to still further features in the described preferred embodiments the linker nucleic acid sequence comprises an IRES or encodes a protease cleavage recognition site.

According to still further features in the described preferred embodiments the TNF alpha is a secreted TNF alpha.

According to still further features in the described preferred embodiments the TNF alpha is a non-secreted TNF alpha.

According to still further features in the described preferred embodiments the cancer-specific promoter is selected from the group consisting of IGF-1, IGF-2 P3 and IGF-2 P4.

According to still further features in the described preferred embodiments the at least one additional nucleic acid sequence comprises two nucleic acid sequences each independently comprising a cancer specific promoter, and whereas the TNF alpha encoding sequence being under the expression control of one cancer specific promoter and the diphtheria toxin encoding sequence being under the expression control of another cancer specific promoter According to still further features in the described preferred embodiments the two cancer specific promoters are identical.

According to another aspect of the present invention there is provided a nucleic acid construct system comprising:
(a) a first nucleic acid construct which comprises:
(i) a first nucleic acid sequence encoding TNF alpha;
(ii) a second nucleic acid sequence comprising a first cancer specific promoter sequence;
the TNF alpha encoding sequence being under an expression control of the first cancer specific promoter sequence;
(b) a second nucleic acid construct which comprises:
(i) a third nucleic acid sequence encoding a Diphtheria toxin;
(ii) a fourth nucleic acid sequence comprising a second cancer specific promoter sequence;
the Diphtheria toxin encoding sequence being under an expression control of the second cancer specific promoter sequence.

According to still further features in the described preferred embodiments each of the first and second cancer specific promoter sequences is selected from the group consisting of IGF-1, IGF-2 P3 and IGF-2 P4.

According to still further features in the described preferred embodiments the first and second cancer specific promoter sequences are identical.

According to still further features in the described preferred embodiments the first and second cancer specific promoter sequences are different.

According to yet another aspect of the present invention there is provided a method of treating a cancer in a subject in need thereof, the method comprising administering to cancer cells of the subject a therapeutically effective amount of any of the nucleic acid constructs, thereby treating the cancer in the subject.

According to still another aspect of the present invention there is provided a method of treating a cancer in a subject, the method comprising administering to cancer cells of a subject in need thereof a therapeutically effective amount of any of the nucleic acid construct systems, thereby treating the cancer in the subject.

According to still further features in the described preferred embodiments the cancer cells are resistant to TNF-α or Diphtheria toxin.

According to still further features in the described preferred embodiments the method further comprising treating the subject with a chemotherapy or a radiation therapy.

According to an additional aspect of the present invention there is provided a pharmaceutical composition comprising, as an active ingredient the any of the nucleic acid constructs and a pharmaceutically acceptable carrier or diluent.

According to yet an additional aspect of the present invention there is provided a pharmaceutical composition comprising, as an active ingredient any of the nucleic acid construct systems and a pharmaceutically acceptable carrier or diluent.

According to still further features in the described preferred embodiments the pharmaceutical composition further comprising a transfection agent.

According to still an additional aspect of the present invention there is provided use of any of the nucleic acid construct for the manufacture of a medicament identified for treating cancer According to a further aspect of the present invention there is provided use of any of the nucleic acid construct systems for the manufacture of a medicament identified for treating cancer.

According to still further features in the described preferred embodiments, wherein the medicament further comprising an anti-cancer drug.

The present invention successfully addresses the shortcomings of the presently known configurations by providing nucleic acid constructs which can be used to treat cancer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a—The coding sequence of TNFα (nucleic acid sequence—SEQ ID NO:4; amino acid sequence—SEQ ID NO: 18) is under the transcriptional control of the H19 promoter (H19 promo) sequence (SEQ ID NO:3). FIG. 1b—The coding sequence of TNFα (SEQ ID NO:4) and DTA (SEQ ID NO:1) is under the transcriptional control of the H19 promoter sequence (SEQ ID NO:3). IRES—ECMV-derived IRES; Kana (R)—kanamycine resistance gene;

FIGS. 5a-i are graphs depicting the reduction of luciferase activity in ovarian (ES-2, TOV-122D, SK-OV3), pancreatic (L3.6PL, CRL2119, and CRL2547), bladder (T-50, T24P), and hepatocellular carcinoma (Hep3B) cell lines following co-transfection with the pH19-DTA (DTA, blue diamonds), pH19-TNFα (TNF, pink squares) or pH19-TNF-IRES-DTA (TNF-DTA, green triangles) vectors. The killing potential of the pH19-DTA vector, the pH19-TNFα vector or the pH19-TNF-IRES-DTA vector in ES-2 (FIG. 5a), TOV-122D (FIG. 5b), SK-OV3 (FIG. 5c), L3.6PL (FIG. 5d), CRL2119 (FIG. 5e), CRL2547 (FIG. 5f), T-50 (FIG. 5g), T24P (FIG. 5h) and HEP3B (FIG. 5i) cells was measured as a reduction of LucSV40 activity. Cells were co-transfected with 2 μg/well of LucSV40 and the indicated concentrations of pH19-DTA, pH19-TNFα, or pH19-TNF-IRES-DTA vectors. As a control (for 100% luciferase activity) each cell line was transfected with LucSV40 alone. Transfection experiments were stopped after 48 hours and reporter gene activity was assessed. The reduction in the LucSV40 activity in the co-transfected cells was compared to the activity of LucSV40 transfected cells. Note the significant reduction in luciferase activity in all tested cell lines following transfection with the pH19-TNF-IRES-DTA vector, demonstrating the potent killing effect of the combined vector.

FIG. 6a-TNFα RT-PCR analysis using primers 5'-GCCATTGGC-CAGGGC3' (SEQ ID NO:14) and 5'-CGCCAC-CACGCTCTTCT3' (SEQ ID NO:15). FIG. 6b-GADP RT-PCR analysis using primers 5'-GGCTCTCCAGAACATCATCCCTGC-3' (SEQ ID NO:16) and 5'-GGGTGTCGCTGTTGAAGTCAGAGG-3' (SEQ ID NO:17). Lane 1—cells transfected with 1.5 μg/ml of a control plasmid luc 1; Lane 2—cells transfected with 0.02 μg/well of the pH19-TNFα plasmid; Lane 3—cells grown in the presence of 10 ng/ml of the TNFα protein in the culture medium; Lane 4—cells transfected with 0.02 μg/well of the pH19-TNF-IRES-DTA plasmid; Lane 5—cells grown in the presence of 100 ng/ml of the TNFα protein in the culture medium; Lane 6—untreated cells; and Lane 7—negative control for RT-PCR reaction (i.e., no RNA). The positions of the TNFα and the GADP internal control PCR products are marked (black arrows). "M"—a 100-bp molecular weight marker.

FIG. 7a—The mean fold increase in tumor size following treatment with the pH19-TNF-IRES-DTA, pH19-TNFα, pH19-DTA and pH19-Luc vectors ("mean fold increase" stands for the ratio between the final mean volume to the initial mean volume). FIG. 7b—The tumor growth progression (TPG) in the pH19-TNF-IRES-DTA, pH19-TNFα, pH19-DTA and pH19-Luc treated tumors. [TPG=(Vf/Vi×100)−100] wherein Vf=initial volume and Vf=final volume.

DESCRIPTION OF THE PREFERRED EMBODIMENTS

Figure 1A:
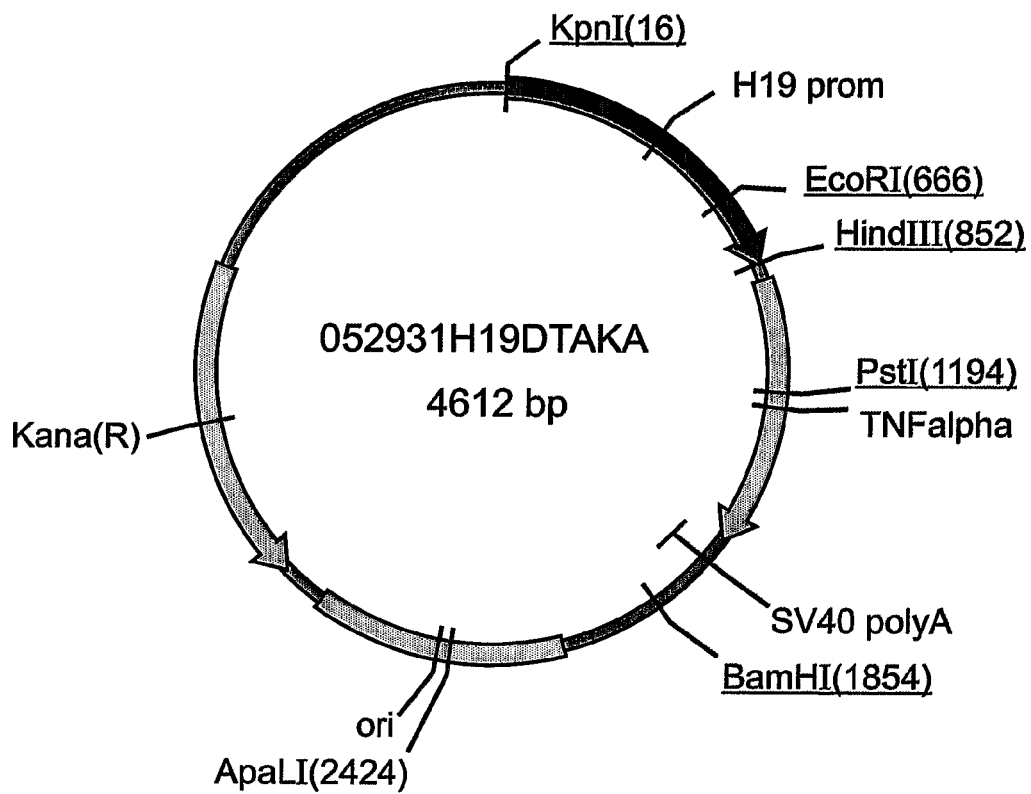
FIG. 1a-b are schematic illustrations depicting the construction of the pH19-TNFα (FIG. 1a) and the pH19-TNFα-IRES-DTA (FIG. 1b) expression vectors.

The present invention is of nucleic acid constructs which can be used to treat cancer.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

A major obstacle to cancer therapy is the problem of selectivity; that is, the ability to inhibit the multiplication of tumor cells, while leaving unaffected the function of normal cells. Thus, more effective treatment methods for therapy and prophylaxis of cancer are needed.

The use of gene therapy in cancer treatment presents many of the same disadvantages as other therapeutic approaches, such as chemotherapy and radiation therapy. Problems with current state-of-the-art gene therapy strategies include the inability to deliver the therapeutic gene specifically to the target cells. This leads to toxicity in cells that are not the intended targets. For example, manipulation of the p53 gene suppresses the growth of both tumor cells and normal cells, and intravenous administration of tumor necrosis factor alpha (TNF-alpha) induces systemic toxicity with such clinical manifestations as fever and hypertension.

Attempts have been made to overcome these problems. These include the use of tissue-specific receptors to direct the genes to the desired tissues, the use of heat or ionizing radiation inducible enhancers and promoters, and the use of tissue-specific promoters to limit gene expression to specific tissues to enhance expression of the therapeutic gene in a temporally and spatially controlled manner. A well-documented example of this latter approach involves the use of the prostate-specific antigen (PSA) promoter in recombinant constructs to direct expression of therapeutic genes to prostatic tissue (See, e.g., U.S. Pat. No. 5,648,478).

PCT Pub. No. WO9918195 teaches the specific expression of heterologous sequences, particularly genes encoding cytotoxic products, in tumor cells under the control of cancer specific promoters (e.g., H19 promoter).

While reducing the present invention to practice the present inventors uncovered that targeted expression of TNFα and Diphtheria toxin A under the expression control of the cancer specific H19 promoter sequence can be used to synergistically reduce volume of tumors expressing same. These findings substantiate the use of targeted expression of TNFα and Diphtheria toxin A in the treatment of various tumors especially those which are refractory to each of these toxins alone.

As is shown in FIGS. 2a-c and 3, and is described in Example 1 of the Examples section which follows, transfection of cells with either the H19-TNFα or the H19-DTA expression vectors resulted in inhibition of cell proliferative activity as determined using the luciferase assay. In addition, as is further shown in FIGS. 4, 5a-i and 6a-b and is described in Examples 1 and 2, co-administration of the H19-TNFα and H19-DTA expression vectors or administration of an expression vector encoding both TNFα and DTA under the transcriptional control of the H119 promoter (pH19-TNF-IRES-DTA) resulted in enhanced inhibition of cancerous cell proliferation. Finally, co-expression of TNF and DTA (pH19-TNF-IRES-DTA) in established models of ovarian cancer tumors resulted in a significant inhibition of tumor growth in vivo (FIGS. 7a-b, Example 3 of the Examples section which follows).

The present therapeutic modality is superior to the co-administration of the protein products of TNFα and Diphtheria toxin (DTX) described by Morimoto et al., 4) in that the tumor-specific expression of these two cytotoxic agents provides a significant safety advantage. Indeed the teachings of Morimoto and co-workers were never practiced in vivo but rather in tissue culture settings which negate the need for cell-specific targeting.

Thus, according to one aspect of the present invention there is provided a nucleic acid construct comprising:

(i) a first nucleic acid sequence encoding TNF alpha;

(ii) a second nucleic acid sequence encoding a Diphtheria toxin; and (iii) at least one additional nucleic acid sequence comprising a cancer specific promoter; said TNF alpha and Diphtheria toxin sequences being under an expression control of said cancer specific promoter.

As used herein "TNF alpha" or (TNFα)" refers to at least an active portion of TNF alpha (e.g., mammalian) which promotes cell death or which may work in cooperation with DTX to promote cell death (measurable using methods which are well known in the art e.g., FACS, MTT and thymidine incorporation). Examples of TNF alpha nucleic acid sequences which can be used in accordance with the present invention, include, but are not limited to, GenBank Accession Nos. NM_000594.2; NT_007592.14; NT_086688.1; AB088112.1; AF043342.1; AF098751.1; AF129756.1; AJ227911.1; AJ249755.1; AJ270944.1; and AL662801.7. See also SEQ ID NO:4.

TNF-alpha sequences of the present invention may be non-secreted [intracellular or membrane bound, see e.g., Corazza Gastroenterology. 2004 September; 127(3):816-25] or secreted. Secreted TNF-alpha comprises a leader sequence [such as set forth in SEQ ID NO:4; the signal sequence locates at the 5' end of the coding sequence (coding for 76 amino acids)].

It will be appreciated that when a construct which includes a secreted TNFα and a toxin under the expression control of the H19 promoter is used to transfect cells the toxin may be active within the cell while the secreted TNF alpha remains in the vicinity of the cell membrane and will bind, at locally high effective concentrations to the TNF-alpha receptor. Without being bound by theory, it is suggested that non-secreted TNF alpha activates intracellular signaling probably by binding to an intracellular receptor (e.g., in the endoplasmic reticulum). As used herein the phrase "Diphtheria toxin" (DT or DTX) refers to at least an active portion of the Diphtheria toxin which promotes cell death or which may work in cooperation with TNFα to promote cell death. DT is comprised of two polypeptide fragments, A and B [Zdanovskaia, M. V.; Zdanovsky, A. G.; Yankovsky, N. K. "Diphtheria toxin NAD affinity and ADP ribosyltransferase activity are reduced at tryptophan 153 substitutions for alanine or phenylalanine." *Research in Microbiology,* 2000, 151, 557-562; Bennet, M. J.; Choe, S.; Eisenberg, D. "Refined structure of dimeric diphtheria toxin at 2.0 angstrom resolution." *Protein Science,* 1994, 3, 1444-1463]. Fragment A (DTA) consists of the catalytic domain (C), whereas fragment B is made up of the receptor domain, (R), and the transmembrane domain, (T). The R domain contains a receptor portion which binds to the HB-EGF receptor on the cell surface [Raab, Gerhard; Klagsbrun, Michael "Heparin-binding EGF-like growth factor" *Biochimica et Biophysica Acta* (*BBA*)/*Reviews on Cancer* 1997, 1333, F179-F199]. The bound toxin then enters the cytoplasm by endocytosis. The C-terminus hydrophobic series of α-sheets, known as the T domain, then embeds itself into the membrane, causing the N-terminus C domain to be cleaved and translocated into the cytoplasm. Once cleaved, the C domain becomes an active enzyme, catalyzing the creation of ADP-ribose-EF-2 from the protein synthesis translocation peptide EF-2 and NAD+. A single C domain can use a cell's entire supply of EF-2 within hours, bringing protein synthesis to a halt, resulting in cell death. Since the present invention envisages recombinant preferably intracellular expression of the toxin the minimal C domain may be used. According to presently known preferred embodiments of this aspect of the present invention the toxin is diphtheria A chain toxin [DTA, e.g., SEQ ID NO:1 (for nucleic acid sequence) and SEQ ID NO:2 (for an amino acid sequence)].

As used herein "a cancer specific promoter" refers to any promoter sequence which is active in an adult subject (i.e., fetal or post natal) only in cancer cells. The selection of the promoter sequence will of course depend on the targeted cancer cell population which requires the selected promoter to be active (see below). Typically a cancer-specific promoter is from regulatory regions of genomically imprinted genes that are expressed in cancer. Regulatory regions from genomically imprinted genes that are expressed in cancer cells include but are not limited to the H19 promoter and enhancer, and the IGF-2 P3 and P4 promoter.

Described herein are H19 regulatory sequences that can be used to direct the tumor cell specific expression of TNFα and DTX (i.e., heterologous genes). These H19 regulatory sequences include the upstream H19 promoter region and/or the downstream H19 enhancer region. The nucleotide sequence of one H19 promoter region is shown in SEQ ID NO: 19. This 831 nucleotide sequence extends from −837 to −7 nucleotides from the cap site (as described in Brannan et al. 1990. Mol Cell biol 10, 28-36). A consensus TATA sequence occurs at nucleotides −27 to −35. Two consensus AP2 binding sites (8/9 matches) occur at approximately −500 and −40 nucleotides upstream from the initiation of transcription. When placed upstream of the coding region for a heterologous gene, approximately 831 base pairs of the regulatory region is sufficient to direct expression of the operatively linked heterologous gene in cancer cells that also express endogenous H19. Additionally, another H19 promoter region between nucleotides −819 to +14 (SEQ ID NO: 19) is also sufficient to direct expression of the operatively linked heterologous gene in cancer cells.

The downstream enhancer region of the human H19 gene can optionally be added to an H19 promoter/heterologous gene construct in order to provide enhanced levels of tumor cell-specific expression (SEQ ID NOs: 20-22). As expected from an enhancer sequence, the downstream enhancer is able to exert its effect when placed in either reverse or direct orientation (relative to the orientation of the H19 enhancer in the endogenous H19 gene) downstream from the coding region of a heterologous gene under the control of the H19 promoter. Additionally, fragments of this enhancer containing the sequences as shown in FIGS. 6, 7A, 7B and 8A-8C (SEQ ID NOs: 20-22) may also be used to facilitate gene expression.

The expression of the IGF-1 gene has been associated with lung cancer and breast cancer. An example of an IGF-1 promoter sequence include the nucleic acid sequence between nucleotides 1 to 1630 of the human IGF-1 gene sequence (GENBANK Accession No. M12659 M77496; Rotwein et al., 1986, J. Biol. Chem. 261:4828-4832).

The IGF-2 gene product is expressed using one of three different promoter regions (P3 and P4). The P3 promoter has been implicated in hepatocarcinoma. It has also been discovered that the imprinted P4 promoter (nucleotide sequence −546 to +102 of the IGF-2 gene (GenBank Accession No. NC_000011) and P3 promoter (nucleotide sequence −1229 to +140 of IGF-2 gene) are activated in human bladder cancer cells, and may be used to direct expression of an operatively linked heterologous gene to tumor cells. The IGF-2 P3 and P4 promoters may be used in combination with the H19 enhancer or active fragments thereof.

These regulatory sequences from genomically imprinted and non-imprinted genes that are expressed in cancer cells can be further delineated to define the minimal regulatory sequences required to obtain the desired tumor specific expression. For example, the promoter region may be altered by additions, substitutions or deletions and assayed for retention of tumor specific expression function. Various portions of the H19 downstream enhancer may be tested individually for the ability to enhance transcription from the H19 promoter.

Alterations in the regulatory sequences can be generated using a variety of chemical and enzymatic methods which are well known to those skilled in the art. For example, regions of the sequences defined by restriction sites can be deleted. oligonucleotide-directed mutagenesis can be employed to alter the sequence in a defined way and/or to introduce restriction sites in specific regions within the sequence. Additionally, deletion mutants can be generated using DNA nucleases such as Bal31 or ExoIII and S1 nuclease. Progressively larger deletions in the regulatory sequences are generated by incubating the DNA with nucleases for increased periods of time (See references at background to the Examples section, for a review of mutagenesis techniques).

The altered sequences are evaluated for their ability to direct tumor specific expression of heterologous coding sequences in appropriate host cells. It is within the scope of the present invention that any altered regulatory sequences which retain their ability to direct tumor specific expression be incorporated into the nucleic acid constructs of the present invention for further use.

As used herein the phrase "being under an expression control" refers to the transcription of the coding sequences of TNFα gene or the Diphtheria toxin from the cancer-specific promoter sequence which is operably-linked thereto to regulate their expression pattern (including spatial and temporal expression pattern).

As used herein the phrase "operably linked" refers to the positioning of the TNFα gene or the Diphtheria toxin coding sequences such that they are linked to the regulatory sequence (i.e., the promoter) in a manner which allows expression of the heterologous genes to be directed by the regulatory sequence As used herein the phrase "nucleic acid sequence" refers to a nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

All the above described nucleic acid sequences (and more as is further described hereinbelow) are ligated into at least one nucleic acid construct.

The nucleic acid construct of the present invention is preferably suitable for mammalian cell expression.

Transcription of TNF alpha and DTX may be governed by a single cancer specific promoter sequence. In this case the TNF alpha and DTX coding sequences may be transcriptionally linked via a linker nucleic acid sequence.

Such a linker nucleic acid sequence may encode a protease cleavage recognition site, such that the TNF alpha and DTX are translated as a single polypeptide which is cleaved to produce two separate polypeptides. In this case however, measures are taken to use a site recognized by an intracellular protease.

Alternatively transcriptional link may be achieved by the use of an internal ribosome entry site (IRES) sequence. The use of bicistronic vectors is described in Example 1 of the Examples section which follows). Bicistronic vectors are readily available such as for example from Millegen, Q-Bio-Gene (e.g., pAdenoVator™-CMV5-IRES-GFP and pAdenoVator™-CMV5-IRES-BFP) Clontech (e.g., pIRES1neo and pIRES2hyg).

Two promoter vectors may be alternatively constructed [see e.g., Kyung-Jin Kim (2004) Protein Science 13:1698-1703]. In this case, the promoter sequences may be identical or different. When different promoter sequences are used (e.g., different regulatory sequences of a single gene or of different genes), measures are taken to use sequences which confer synchronized expression at about similar levels. Transcriptional assays (e.g., Luciferase reporter assay) may be used to select such sequences (see gene expression assays further below).

The present invention also contemplates a nucleic acid construct system of which a preferred configuration comprises:

(a) a first nucleic acid construct which comprises:
  (i) a first nucleic acid sequence encoding TNF alpha;
  (ii) a second nucleic acid sequence comprising a first cancer specific promoter sequence;
  the TNF alpha encoding sequence being under an expression control of the first cancer specific promoter sequence;
(b) a second nucleic acid construct which comprises:
  (i) a third nucleic acid sequence encoding a Diphtheria toxin;
  (ii) a fourth nucleic acid sequence comprising a second cancer specific promoter sequence; the Diphtheria toxin encoding sequence being under an expression control of the second cancer specific promoter sequence.

Although a 1:1 ratio is presently preferred, the ratio between the first nucleic acid construct and the second nucleic acid construct can be different from 1:1 and may be empirically determined.

The nucleic acid construct (also referred to herein as an "expression vector") or construct system of the present invention may include additional sequences that render this vector suitable for replication and integration in prokaryotes, eukaryotes, or preferably both (e.g., shuttle vectors). In addition, a typical cloning vector may also contain transcription and translation initiation sequences, transcription and translation terminators, and a polyadenylation signal.

Enhancer elements can stimulate transcription up to 1,000-fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus or human or murine cytomegalovirus (CMV) and the long tandem repeats (LTRs) from various retroviruses, such as murine leukemia virus, murine or Rous sarcoma virus, and HIV. See Gluzman, Y. and Shenk, T., eds. (1983). Enhancers and Eukaryotic Gene Expression, Cold Spring Harbor Press, Cold Spring Harbor, N.Y., which is incorporated herein by reference. H19 enhancer sequences which can be used in accordance with this aspect of the present invention include but are not limited to those described in U.S. Pat. No. 6,306,833 (SEQ ID NOs: 20-22).

In the construction of the expression vector, the promoter is preferably positioned approximately the same distance from the heterologous transcription start (of the TNFα, or the Diphtheria toxin) site as it is from the transcription start site in its natural setting. As is known in the art, however, some variation in this distance can be accommodated without loss of promoter function.

Polyadenylation sequences can also be added to the expression vector in order to increase the efficiency of TNF alpha/toxin mRNA translation. Two distinct sequence elements are required for accurate and efficient polyadenylation: GU- or U-rich sequences located downstream from the polyadenylation site and a highly conserved sequence of six nucleotides, namely AAUAAA, located 11-30 nucleotides upstream of the site. Termination and polyadenylation signals suitable for the present invention include those derived from SV40.

In addition to the embodiments already described, the expression vector of the present invention may typically contain other specialized elements intended to increase the level of expression of cloned nucleic acids or to facilitate the identification of cells that carry the recombinant DNA. For example, a number of animal-viruses contain DNA sequences that promote extra-chromosomal replication of the viral genome in permissive cell types. Plasmids bearing these viral replicons are replicated episomally as long as the appropriate factors are provided by genes either carried on the plasmid or with the genome of the host cell.

The expression vector of the present invention may or may not include a eukaryotic replicon. If a eukaryotic replicon is present, the vector is capable of amplification in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, and pNMT81, which are available from Invitrogen, pCI which is available from Promega, pMbac, pPbac, pBK-RSV and pBK-CMV, which are available from Strategene, pTRES which is available from Clontech, and their derivatives. These may serve as vector backbone for the constructs of the present invention.

Expression vectors containing regulatory elements from eukaryotic viruses such as retroviruses can be also used. SV40 vectors include pSVT7 and pMT2, for instance. Vectors derived from bovine papilloma virus include pBV-1MTHA, and vectors derived from Epstein-Barr virus include pHEBO and p2O5. Other exemplary vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells. These may serve as vector backbone for the constructs of the present invention.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinarily skilled artisan and as such, no general description of selection considerations is provided herein. For example, bone marrow cells can be targeted using the human T-cell leukemia virus type I (HTLV-I) and kidney cells may be targeted using the heterologous promoter present in the baculovirus *Autographa californica* multiple nucleopolyhedrovirus (AcMNPV), as described by Liang, C. Y. et al. (2004). High efficiency gene transfer into mammalian kidney cells using baculovirus vectors. Arch Virol 149, 51-60.

Recombinant viral vectors are useful for in vivo expression of the genes of the present invention since they offer advantages such as lateral infection and targeting specificity. Lateral infection is inherent in the life cycle of retrovirus, for example, and is the process by which a single infected cell produces many progeny virions that bud off and infect neighboring cells. The result is the rapid infection of a large area of cells, most of which were not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Currently preferred in vivo nucleic acid transfer techniques (i.e., in vivo gene therapy) include transfection with viral or non-viral constructs, such as adenovirus, lentivirus, Herpes simplex I virus, or adeno-associated virus (AAV) and lipid-based systems. Plasmid DNA can be delivered with the help of, for example cationic polymers, cationic liposomes (e.g. lipofectin, cholesterol derivatives such as D.D.A.B. and cationic phospholipids) or derivatized (e.g., antibody conjugated), polylysine conjugates, gramicidin S, artificial viral envelopes or other such intracellular carriers, as well as direct injection of the naked gene construct, electroporation or $CaPO_4$ precipitation carried out in vivo as well as polyethylenimine-based non-viral gene delivery systems (which is currently preferred). Current reviews on nucleic acid transfer and expression systems for cancer gene therapy include Lungwitz (2005) Eur. J. Phar. Biopharm. 60 (2):247-66; Aigner (2006) J. Biotechnol. 254:12-25; Christopher and Wong (2006) Curr. Pharm. Des. 1995-2006; and Wolff (2005) Acta Myol. 24:202-8.

As mentioned the nucleic acid constructs of the present invention (described above) can be used to treat hyperproliferative diseases in which induction of cell death is therapeutically beneficial, such as cancer.

Thus, according to another aspect of the present invention there is provided a method of treating cancer in a subject. The method is effected by administering to cancer cells of a subject in need thereof a therapeutically effective amount of the above described nucleic acid construct and/or nucleic acid constructs system, thereby treating the cancer in the subject.

The phrase "a subject in need thereof" refers to a mammalian subject, preferably a human subject at any age who has been diagnosed with cancer.

The term "treating" refers to inhibiting or arresting the development of a pathology (e.g., cancerous disease) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. Preferably, the term "treating" refers to alleviating or diminishing a symptom associated with a cancerous disease. Preferably, treating cures, e.g., substantially eliminates, the symptoms associated with cancer.

Cancers that are preferably treated with the nucleic acid constructs of the present invention include, but are not limited to, Pediatric solid tumors, Wilms' tumor, Hepatoblastoma, Embryonal rhabdomyosarcoma, Germ cell tumors and trophoblastic tumors, Testicular germ cells tumors, Immature teratoma of ovary, Sacrococcygeal tumors, Choriocarcinoma, Placental site trophoblastic tumors, Epithelial adult tumors, Bladder carcinoma, Hepatocellular carcinoma, Ovarian carcinoma, Cervical carcinoma, Lung carcinoma, Breast carcinoma, Squamous cell carcinoma in head and neck, Esophageal carcinoma, Neurogenic tumors, Astrocytoma, Ganglioblastoma, Neuroblastoma, Preferably the tumor is bladder carcinoma.

The type of cancer to be treated will dictate the type of cancer-specific promoter used. Essentially, the selected cancer specific promoter is to be active (preferably mediates high expression) in the cancer cells.

Gene expression assays may be effected to determine activation of the cancer specific promoter in the cancer cell. These may include in vitro, in vivo and in situ assays (see U.S. Pat. No. 6,306,833). In situ, i.e., directly upon tissue sections (fixed and/or frozen) of patient tissue obtained from biopsies or resections, such that no nucleic acid purification is necessary. Nucleic acid reagents such as those described above may be used as probes and/or primers for such in situ procedures (See, for example, Nuovo, G. J., 1992, "PCR In Situ Hybridization: Protocols And Applications", Raven Press, N.Y.).

An alternative method to determine if a cell type or tumor will be capable of specifically activating expression constructs containing the particular regulatory regions operatively linked to a heterologous gene is to actually transfect such expression constructs into the cell. For these purposes, a marker gene is located down-stream of the regulatory sequence. A positive result in an assay for the marker gene product reveals that the cell or cell line is capable of activating expression from the regulatory regions.

Using these techniques, exemplary tumor types with activated H19 expression are listed in Table 1 below.

TABLE 1

A. Pediatric solid tumors

1. Wilm's tumor
2. Hepatoblastoma
3. Embryonal rhabdomyosarcoma

B. Germ cell tumors and trophoblastic tumors

1. Testicular germ cell tumors
2. Immature teratoma of ovary
3. Sacrococcygeal tumor
4. Choriocarcinoma
5. Placental site trophoblastic tumors C. Epithelial adult tumors 1. Bladder carcinoma
2. Hepatocellular carcinoma
3. Ovarian carcinoma
4. Cervical carcinoma
5. Lung carcinoma
6. Breast carcinoma
7. Squamous cell carcinoma in head and neck
8. Esophageal carcinoma
9. Thyroid carcinoma D. Neurogenic tumors 1. Astrocytoma
2. Ganglioblastoma
3. Neuroblastoma Accordingly, the above cancers are treatable by the methods of the invention. In fact, any tumors which activate H19 expression may be treated by the methods of the invention.

Additionally, the aforementioned techniques may be applied to determine tumors that activate the IGF-1, and the IGF-2 P3 and P4 promoters. Such tumors are also treatable by the methods of the invention. For example, IGF-2 is activated in childhood tumors, such as Wilm's tumors, rhabdomyosarcomas, neuroblastomas and hepatoblastomas.

It will be appreciated that those cancers which are refractory to DTX or TNF-alpha treatment may still and even preferably treated in accordance with the present invention as the synergistic effect of the combined treatment with both DTX and TNF is expected to mediate cell killing even in such types of refractory tumors.

The phrase "a therapeutically effective amount" refers to an amount of the nucleic acid construct and/or nucleic acid constructs system of the present invention which is effective to prevent, alleviate or ameliorate symptoms of the pathology (e.g., cancer) or prolong the survival of the subject being treated.

As mentioned, the therapeutically effective amount of the nucleic acid construct and/or nucleic acid constructs system of the present invention is administered to cancer cells of a subject in need thereof using any of the in vivo gene therapy methods described hereinabove.

Though the half-life of TNF alpha is short (20-30 minutes), measures are taken to ensure cytotoxic activity of the constructs of the present invention on cancerous cells only (and not on normal healthy cells).

The nucleic acid constructs of the present invention can be provided to the subject per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Preferably the pharmaceutical composition can also include a transfection agent such as DOTMA, DOPE, and DC-Chol [Tonkinson et al., Cancer Investigation, 14(1): 54-65 (1996)]. A preferred example of a transfection agent is poly(ethylamine) (PEI).

Herein the term "active ingredient" refers to the nucleic acid construct(s) preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, intraarterial, intravesicle (into the bladder) or intraocular injections.

Alternately, one may administer a preparation in a local rather than systemic manner, for example, via injection of the preparation directly into a specific region of a patient's body or by direct administration into a body cavity such as the bladder, uterus etc.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

In order to improve therapeutic efficacy, treatment with the nucleic acid constructs of the present invention may be combined with other anti-cancer therapies, even if the latter were proven not effective in the treatment of such cancers.

Thus, the nucleic acid constructs of the present invention can be used to treat cancer alone or in combination with other established or experimental therapeutic regimens against cancer. It will be appreciated that the synergistic activity of such combination therapy has the potential to significantly reduce the effective clinical doses of such treatments, thereby reducing the often devastating negative side effects and high cost of the treatment.

Therapeutic methods for treatment of cancer suitable for combination with the present invention include, but are not limited to, chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy, and photon beam radiosurgical therapy.

Anti-Cancer Drugs

Anti-cancer drugs that can be co-administered with the constructs of the invention include, but are not limited to: Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofairin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride. Additional antineoplastic agents include those disclosed in Chapter 52, "Antineoplastic Agents" (Calabresi, P. and Chabner, B. A.), and the introduction thereto, pp. 1202-1263, of Goodman and Gilman, The Pharmacological Basis of Therapeutics, Eighth Edition, 1990, McGraw-Hill, Inc. (Health Professions Division).

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Cells—T-24P (ATCC Accession No. HTB-4), Hep3B (ATCC Accession No. HB-8064), TOV-122D (ATCC Accession No. CRL-11731), ES-2 (ATCC Accession No. CRL-1978), SK-OV3 (ATCC Accession No. HTB-77), L3.6PL [Bruns C J, Harbison M T, Kuniyasu H, Eue I, Fidler I J. Neoplasia. 1999 April; 1(1):50-62 In vivo selection and characterization of metastatic variants from human pancreatic adenocarcinoma by using orthotopic implantation in nude mice], HPAC (ATCC Accession No. CRL2119), Panc 10.05 (ATCC Accession No. CRL2547, T-50 (MBT2-t50) a highly metastatic variant of the MBT2 murine bladder carcinoma cell line was provided by Dr. O. Medalia (Sackler Medical School, Tel Aviv University).

Plasmids—H19-DTA-KANA construct (GeneArt GmbH Regensburg D-93053); LucSV40 construct Promega Inc.

Construction of an H19-TNFα expression vector—Subcloning of TNF-alpha (TNFα) into H19-DTA-KANA construct was performed by replacing the DTA sequence (SEQ ID NO: 1) with that of TNFα (SEQ ID NO:4). Briefly, the human TNFα gene and flanking restriction sites were assembled from synthetic oligonucleotides and cloned into a standard cloning vector (pPCRscript) using KpnI and SacI restriction sites. The TNFα reading frame (SEQ ID NO:3) was excised using BspHI and XbaI restriction enzymes and subcloned into the H19-DTA KANA vector which was digested with the NcoI and XbaI restriction enzymes. After transfection of competent bacteria, single colonies were analyzed by site specific PCR. The plasmid DNA was purified from one positive clone. The final construct (as schematically depicted in FIG. 1a; construct sequence is set forth by SEQ ID NO:7) was verified by sequencing using the SV40 polyA [AAACTTGTTTATTGCAGCTTATAATG (SEQ ID NO:5)] and Am5 [GCTCAGGTCTCTGGGGAACTCCTCTCTCTGGGGGGATGGAGAGCGTATGT TAGTAC (SEQ ID NO:6)] primers.

Construction of the pH19-TNF-IRES-DTA plasmid—The introduction of two genetic elements IRES and TNFα reading frame into the plasmid pH19-DTA-KANA was performed by subsequent cloning steps:

(i) The ECMV-derived IRES sequence was generated by PCR amplification using the plasmid pIRES2-EGFP (BD-Bioscience Clontech) as template and a pair of oligonucleotides, introducing NcoI (5') [5'-TTAACCATGGCCCCTCTCCCTCCC-3' (SEQ ID NO:8)] and BspHI (3') [5'-TTAATCATGATGTGGCCATATTATCATCGT-3' (SEQ ID NO:9)] overhangs. The fragment was digested using NcoI and BspHI restriction enzymes and cloned directionally into the plasmid pH19-DTA-KANA (Geneart GmbH) linearized by NcoI restriction digest. After transfection of competent E. coli, single colonies were analyzed by site specific PCR. The plasmid DNA was purified from one positive clone and concentration determined by UV spectroscopy. The positive construct was verified by sequencing.

Figure 1B:
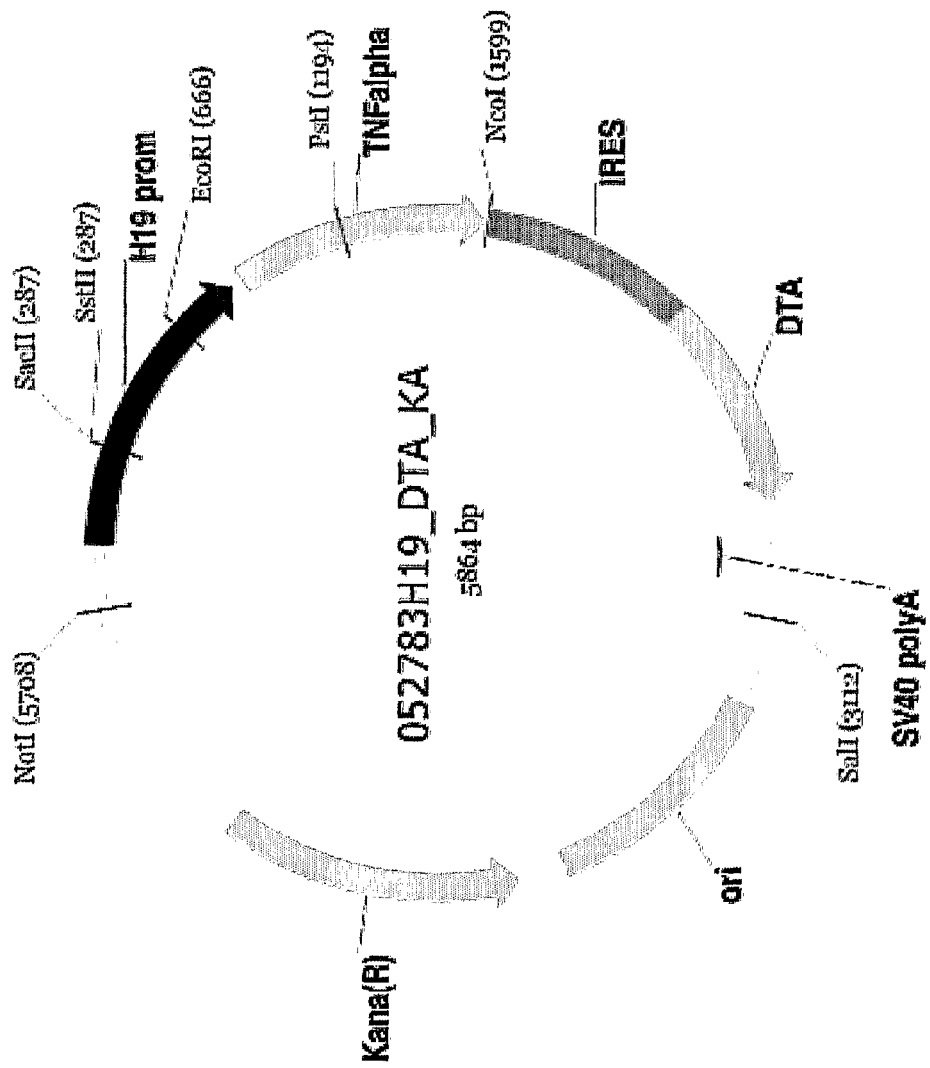

(ii) The human TNFα gene and flanking restriction sites were assembled from synthetic oligonucleotides and cloned into a standard cloning vector (pPCRscript) using KpnI and SacI restriction sites. The TNFα reading frame was excised using BspHI and NcoI restriction enzymes and subcloned into pH19-IRES-DTA-KANA [obtained in step (i)], digested with NcoI. After transfection of competent E. coli, single colonies were analyzed by site specific PCR. The plasmid DNA was purified from one positive clone and concentration determined by UV spectroscopy. The final construct (as schematically depicted in FIG. 1b; construct sequence is set forth by SEQ ID NO:13) was verified by sequencing using the following primers: H19-DTA-1f (825): 5'-GAAAAAGC-CCGGGCTAG-3' (SEQ ID NO:10); H19-DTA-2r (968): 5'-CCCGTGGTACGAAGAAAAG-3' (SEQ ID NO:11); and H19-DTA-4r (711RES): 5'-GACAAACGCACACCGGC-3' (SEQ ID NO:12).

Luciferase assay—Effected according to Manufacturer's protocol (Promega Corp.).

ELISA assay—Effected according to Manufacturer's protocol (Endogen).

Tumor growth in animal model—ES-2 human ovarian cancer cells (2 million cells were injected to each mouse?) were subcutaneously injected into the back of 6-7 weeks old Athymic female mice in order to develop a model for heterotopic ovarian cancer. 10 days following subcutaneous cell inoculation, the mice developed measurable heterotopic tumors. The therapeutic potential of the pH19-TNF-IRES-DTA, pH19-TNFα or pH19-DTA vectors were tested by directly injecting the tumor with 25 µg/tumor of each of the expression vectors. As a control, 25 µg/tumor of pH19-Luc vector was injected.

Example 1

Inhibition of Growth of Cancerous Cells Using the TNFα and/or the Diphtheria Toxin (DTA) Under the Transcriptional Control of H19 Promoter TNFα has a broad spectrum of anticancer activities. However, systemic delivery of the TNFα resulted in limited clinical success, mainly because of severe dose limiting toxic effects. The present inventors have uncovered that this limitation can be overcome by using a gene delivery approach in which the production of TNF protein is controlled by a promoter of genes expressed in cancer cells but not in normal cells. To this end, the present inventors have cloned the TNFα coding sequence under the control of the H19 promoter.

zzyy TNFα and diphtheria toxin A (DTA) trigger DNA fragmentation and target cell lysis with similar kinetics. Protein synthesis inhibition by DTA is not sufficient to target cell lysis. Based on these similarities, DTA and TNFα may either share a common cytolytic pathway or may overlap in their cytolytic pathways. The present inventors have used the pH19-DTA construct in combination with a pH19-TNFα construct to inhibit the growth of cancer cells, as follows.

Experimental Results

Figure 2A:
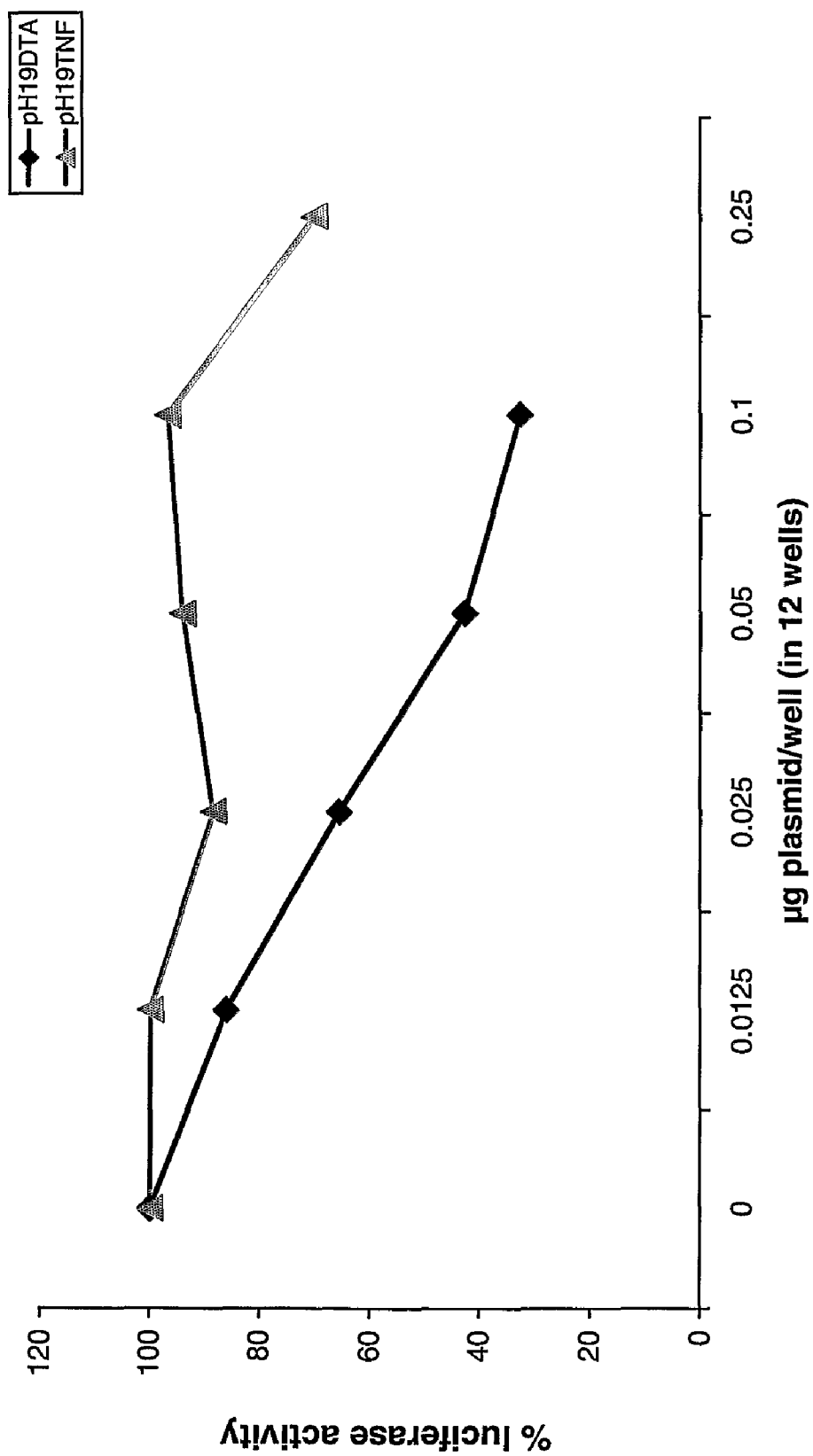
FIGS. 2a-c are graphs depicting the killing potential of the pH19-DTA or pH19-TNFα expression vectors in T24P (FIG. 2a), Hep3B (FIG. 2b) or TOV-122D (FIG. 2c) cell lines as a reduction in luciferase activity. Cells were co-transfected with 2 μg/well of LucSV40 vector and the indicated concentrations of pH119-DTA (diamonds) or pH119-TNFα (triangles). As a control (for 100% luciferase activity) each cell line was transfected with the LucSV40 vector alone. Transfection experiments were stopped after 48 hours and reporter gene activity was assessed. The reduction in the LucSV40 activity in the co-transfected cells was compared to the luciferase activity in cells transfected with the LucSV40 vector alone. Note the significant reduction in luciferase activity in cells transfected with the pH19-DTA vector.
Figure 2B:
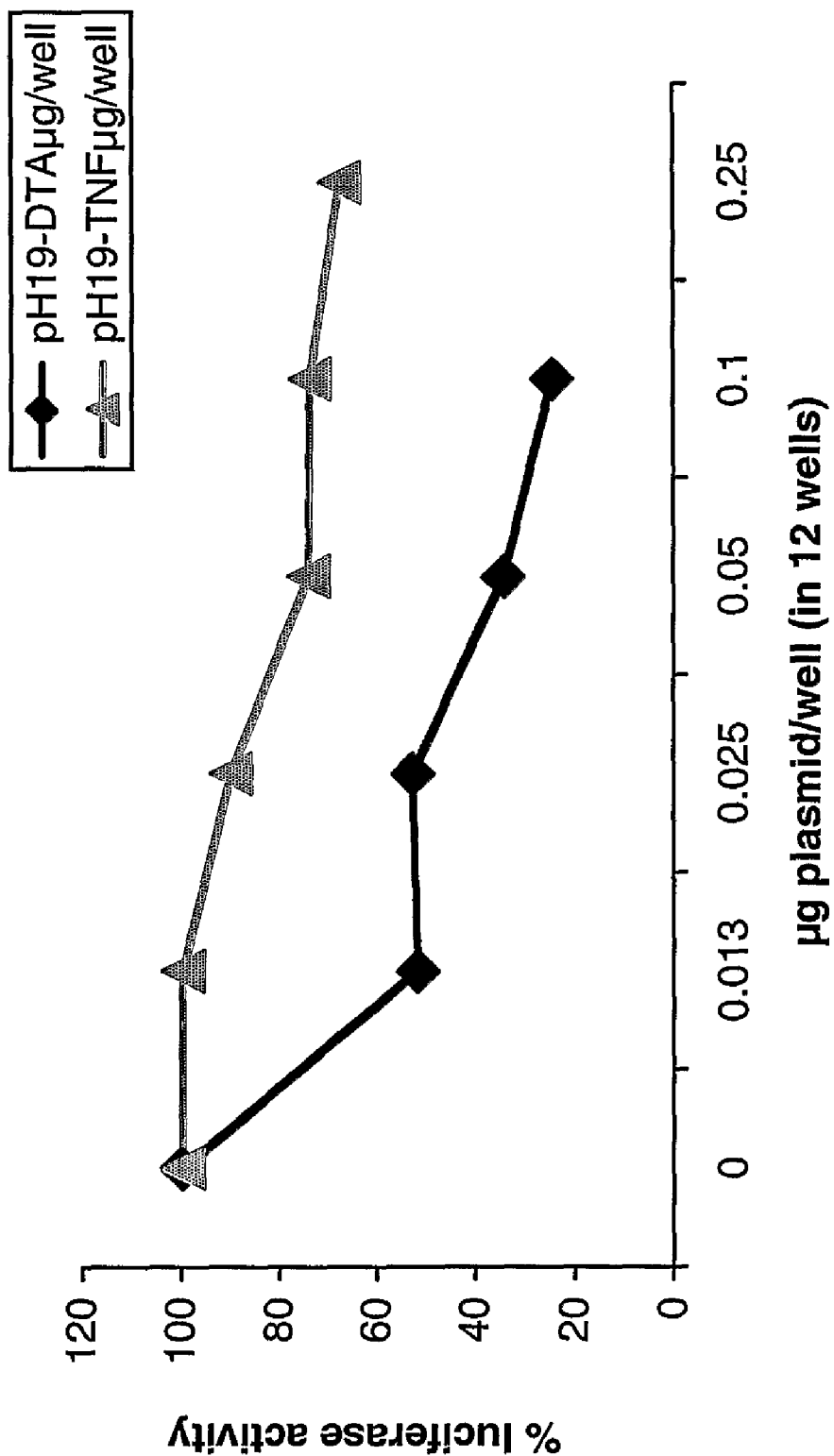
Figure 2C:
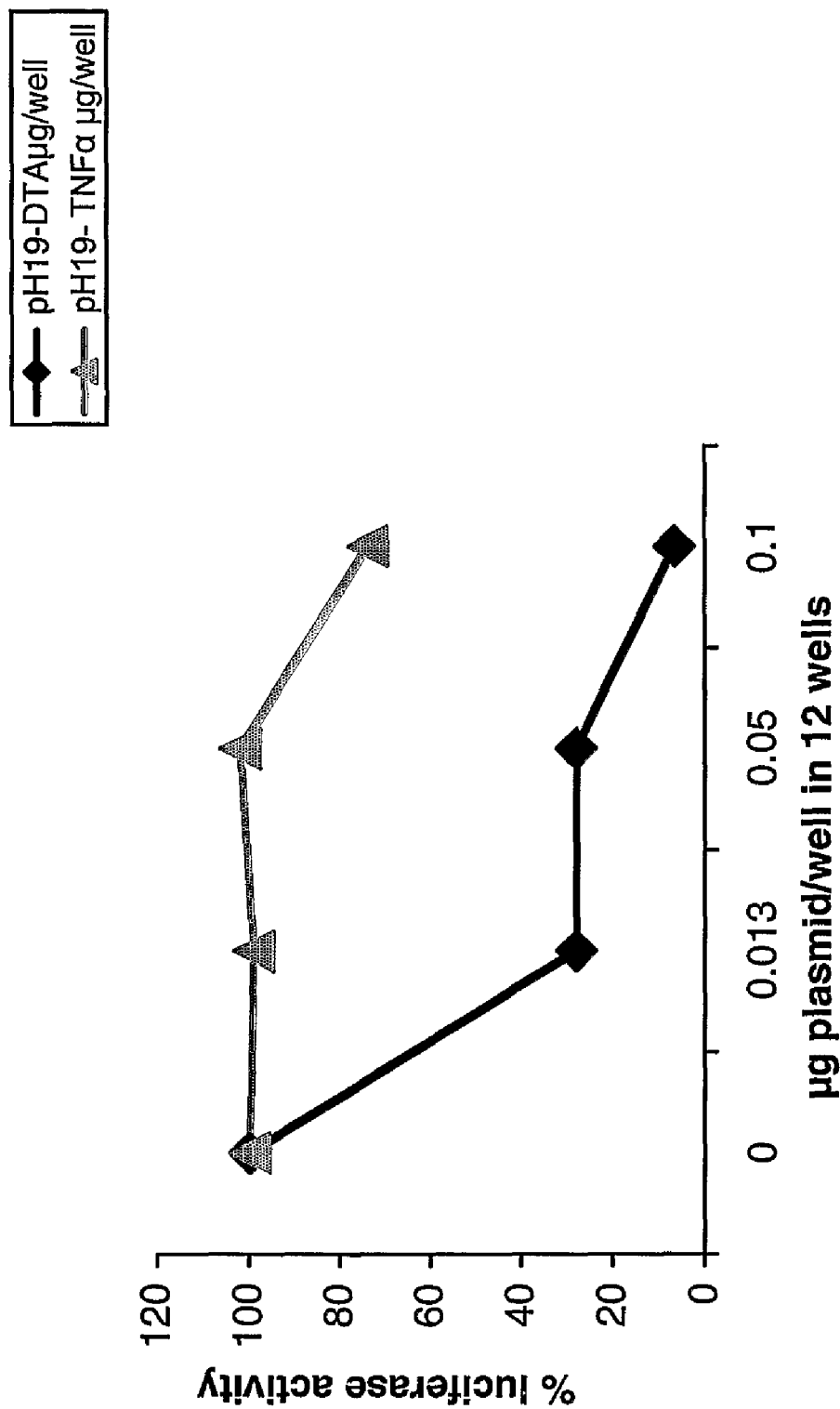

Transfection of cells with either the pH19-DTA or the pH19-TNFαexpression vectors resulted in inhibition of cell proliferative activity—To determine the potential synergistic effect of DTA and TNFα the in-vitro therapeutic potential of either the pH19-DTA or the pH19-TNFα plasmids was tested in T24P, Hep3B and TOV-122D cell lines (FIGS. 2a, 2b and 2c, respectively). Briefly, cells were co-transfected with 2 µg/well of LucSV40 and the indicated concentrations of pH19-DTA or pH19-TNFα plasmids and the decrease in luciferase activity in the presence of the pH19-DTA or pH 19-TNFα plasmids was compared to that observed when the cells were transfected with the LucSV40 plasmid alone (considered as 100% luciferase activity). As is shown in FIGS. 2a-c, a decrease in luciferase activity was detected in all three cell lines when co-transfected with the LucSV40 and either the pH19-DTA or the pH19-TNFα vectors, demonstrating that the H19 promoter is able to drive the expression of the DTA or the TNFα coding sequences and thus reduce LucSV40 activity. In addition, the inhibition caused by the pH19-DTA plasmid was found to be more significant than that caused with the pH19-TNFα vector. Even low concentrations of the pH19-DTA vector as compared to LucSV40 were able to decrease the level of luciferase activity in all tested cell lines. At concentration of 0.0125-0.025 µg/well of DTA containing vector the luciferase total activity induced by 2 µg LucSV40, was reduced. However, relatively high concentrations (0.1 µg/well) of TNFα containing vector caused the reduction of total luciferase activity induced by 2 µg/well LucSV40. As the amount of LucSV40 is much larger than that of the pH19-DTA or pH19-TNFα vector, one can assume that the decrease of luciferase activity is not due to a competition with the pH19-DTA or the pH19-TNFα vector, causing a reduction in the amount of LucSV40 which entered the cells, but a direct consequence of DTA or TNFα activity.

Figure 3:
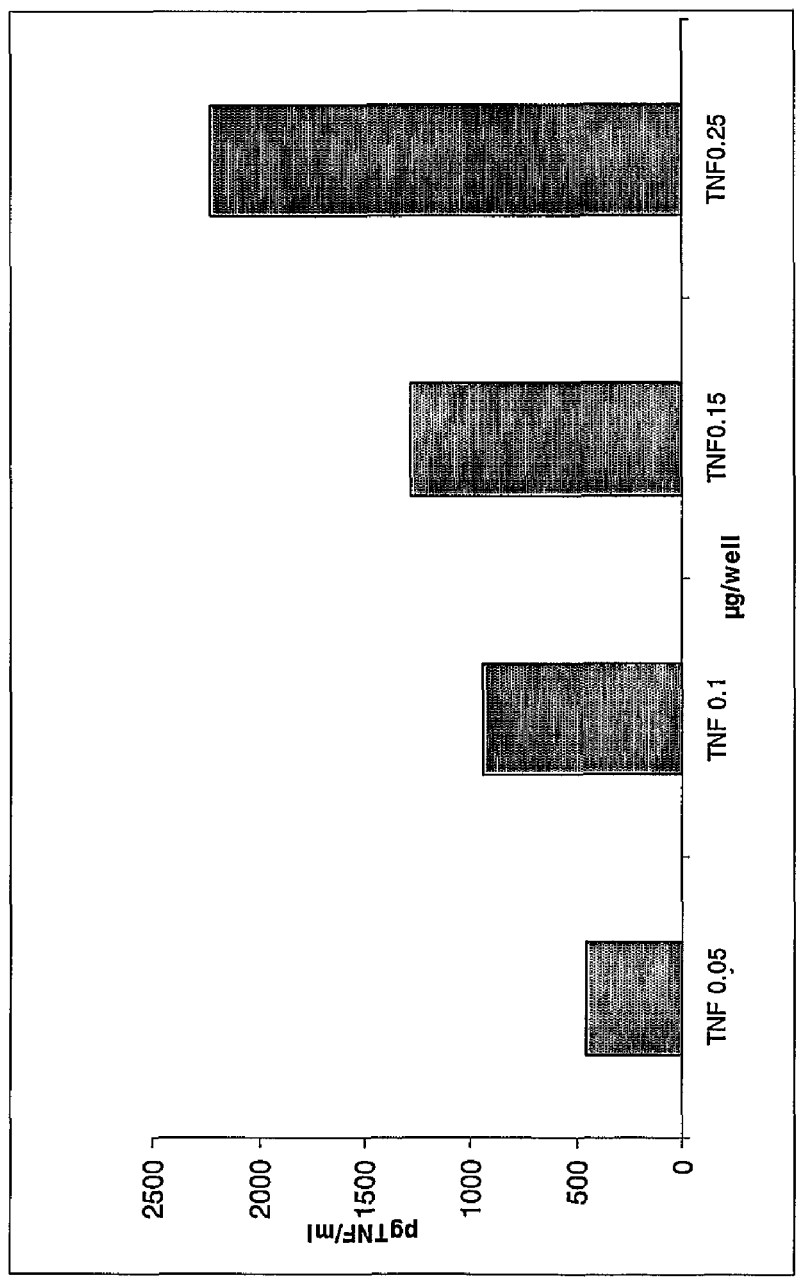
FIG. 3 is a histogram depicting a TNF-specific ELISA assay in TOV-122D cells transfected with the pH19-TNFα expression vector. The concentration of TNFα [measured in picogram (pg) per milliliter (ml)] is shown as a function of the concentration of the pH19-TNFα vector (measured in μg/well) used to transfect the TOV-122D cells. Note that the amount of TNFα secreted protein expressed after transfection of TOV-122D cells proportionally increases with the amount of pH19-TNFα vector used to transfect the cells.

In-vitro expression of the TNF protein from the pH19-TNFα vector—TNF is normally secreted from the cell, and binds to its receptor. As a consequence of this binding, a broad range of cell activities are transduced. To test whether the reduction in the luciferase activity was caused by TNFα expression and secretion from the transformed plasmid, an ELISA assay was employed. Forty-eight hours after transfection of TOV-122D cells with the pH19-TNFα construct, the supernatant was collected and kept at −80° C. till assayed using a TNF-specific ELISA. The amount of TNFα protein was normalized to a standard curve with increased concentrations of TNF. As is shown in FIG. 3, the level of the secreted TNF protein increased along with the increase in concentration of the pH19-TNFα plasmid transfected in the OV-122D cell line. About 2500 pg/ml of TNFα was detected after transfection with 0.25 µg/well of the pH19-TNFα plasmid. A very small amount of TNF was detected in the control plasmid transfected cells (data not shown). These results indicate that the H19 promoter is able to drive the expression of the TNFα gene and that the TNFα protein is secreted to the culture medium.

Figure 4:
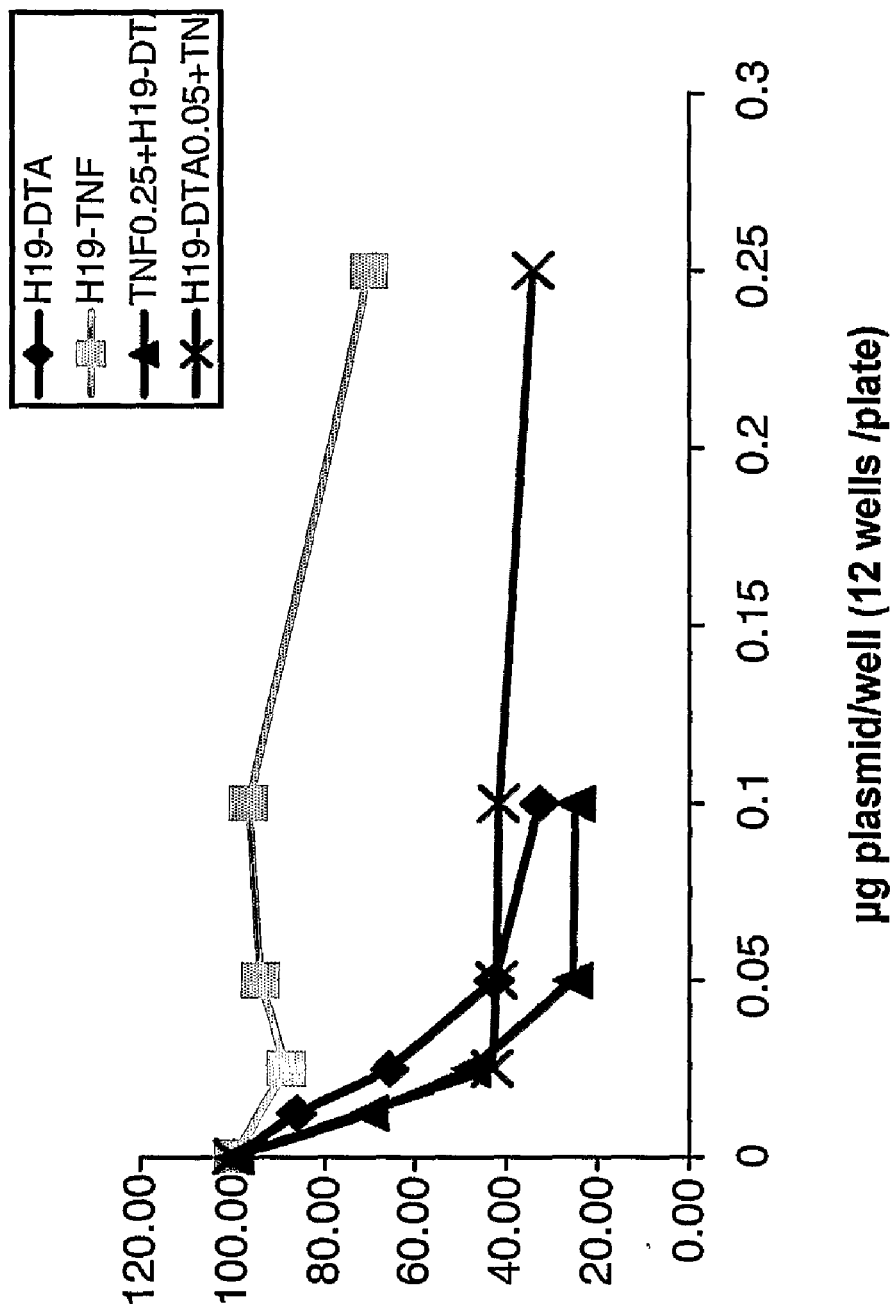
FIG. 4 is a graph depicting the synergistic cytotoxic effect of pH19-DTA and the pH19-TNFα expression vectors on T24P cells. The killing potential of the pH19-DTA (blue diamonds) or pH19-TNFα (pink squares) vectors alone, or the combination of a constant concentration of pH19-DTA with variable concentrations of pH19-TNFα (brown "X") or a constant concentration of pH19-TNFα with variable concentrations of pH19-DTA (green triangles) was measured in T24P cells as a reduction of LucSV40 activity. Cells were co-transfected with 2 μg/well of LucSV40, 0.05 μg/well of pH19-DTA or 0.25 μg/well of pH19-TNFα, and the indicated concentrations or pH19-TNFα or pH19-DTA respectively. As a control (for 100% luciferase activity) cells were transfected with the LucSV40 vector alone. Transfection experiments were stopped after 48 hours and reporter gene activity was assessed. Note the significant reduction in luciferase activity in cells transfected with the pH 19-DTA vector alone or in combination with the pH19-TNFα vector.
Figure 5A:
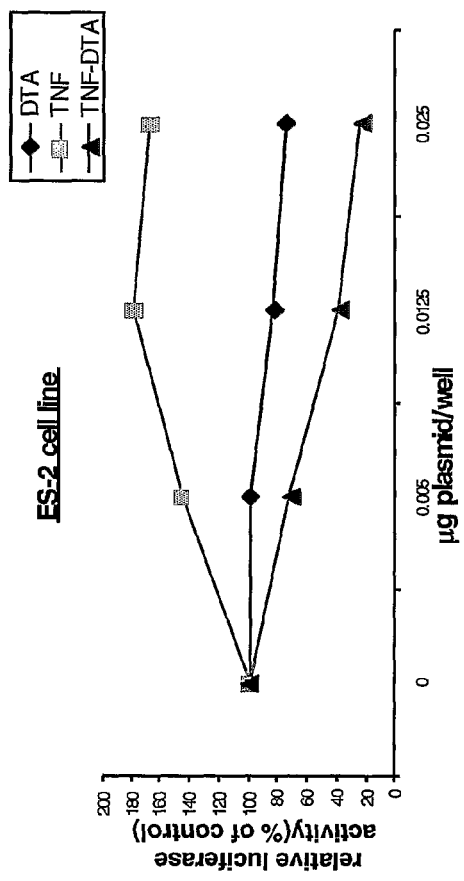
Figure 5B:
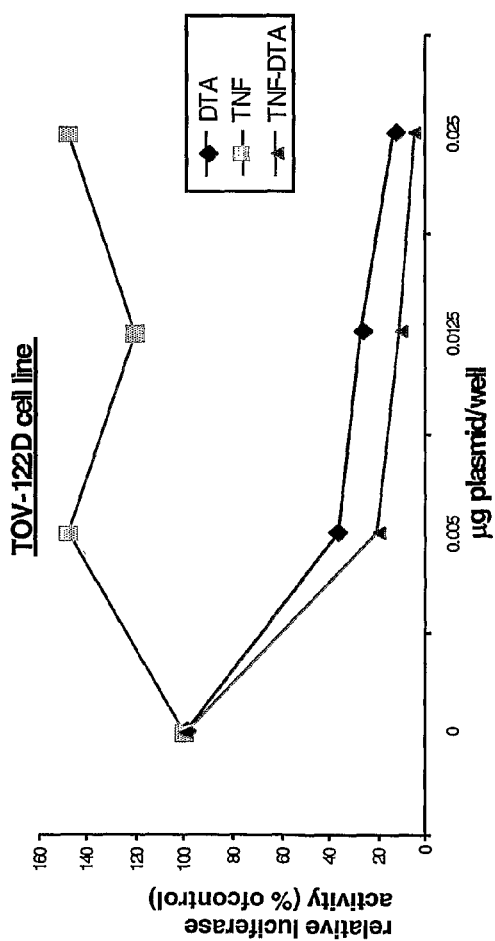
Figure 5G:
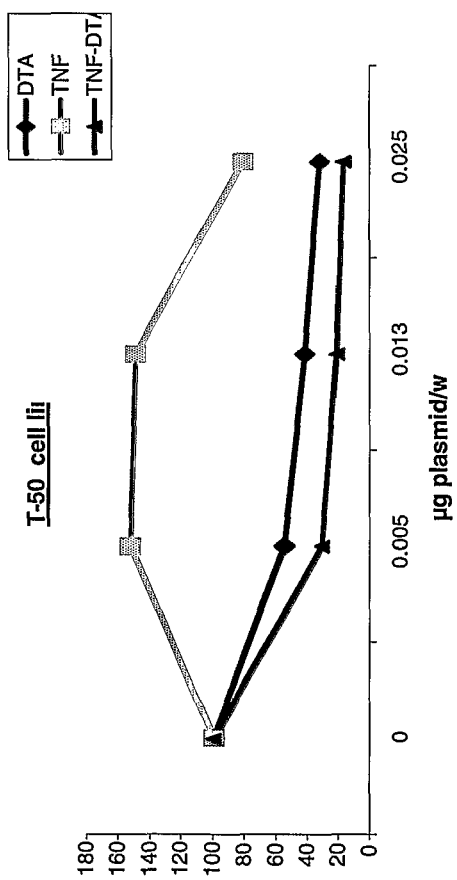
Figure 5H:
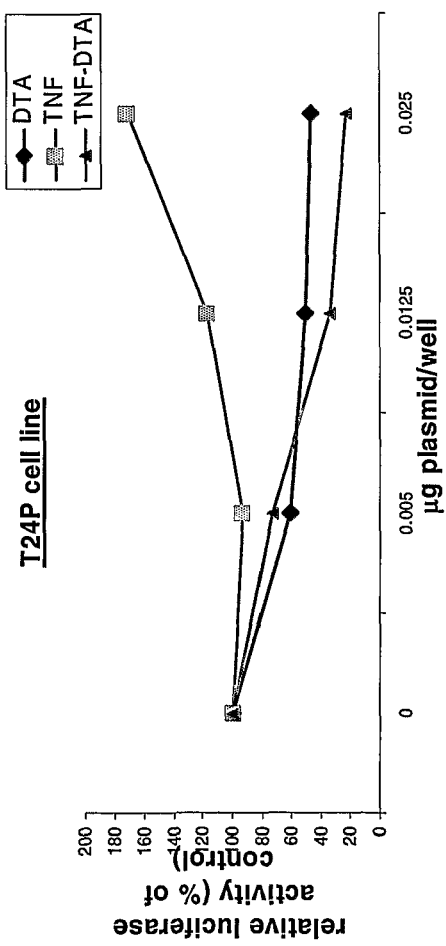
Figure 5I:
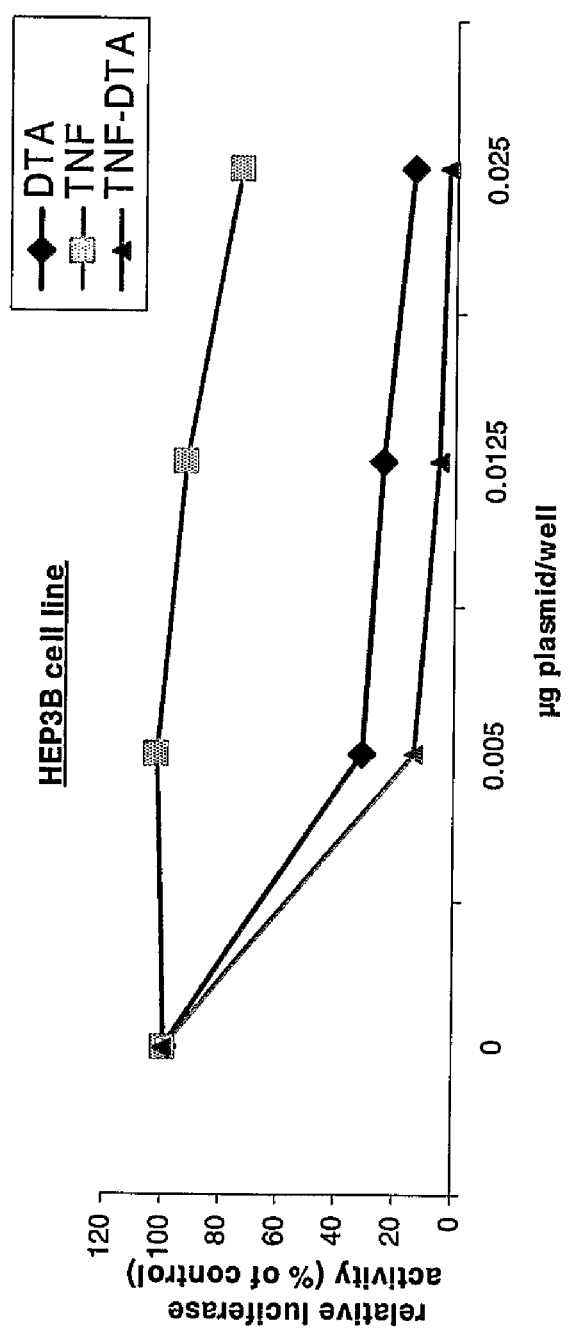

Cytotoxic effect of the combined use of the pH19-DTA and pH-19-TNFα vectors—To determine whether a combined use of the pH19-DTA and the pH19-TNFα vectors will result in enhanced cytotoxicity and synergism in T24P cells, cells were co-transfected with 2 µg/well of LucSV40, a constant concentration of the pH19-DTA (0.05 µg/well) or pH19-TNFα (0.25 µg/well) vectors and the indicated concentrations of pH19-DTA or pH19-TNFα, respectively. Luciferase activity was determined and compared to that of cells transfected with LucSV40 alone. The results presented in FIG. 4 show a decrease in luciferase activity in the co-transfected cell lines with either a constant concentration of pH19-DTA and variable concentrations of pH19-TNFα or a constant concentration pH19-TNFα and variable concentrations of pH19-DTA compared with pH19-DTA or pH19-TNFα vectors alone. A more significant reduction in luciferase activity was noted by using 0.25 µg/well of pH19-TNFα and 0.1 µg/well of pH19-DTA construct.

Altogether, these results demonstrate enhanced cytotoxicity and synergism in inhibition of cancerous cell growth when using both expression vectors in which the DTA or TNFα are driven by the H19 promoter. This is especially important in tumors which are resistant to a variety of drugs including DTA or TNF (e.g., SK-OV3 ovarian cells).

Example 2

The Cytotoxic Effect of TNFα and DTA Coding Sequences Under the Control of the H19 Promoter in Cancerous Cell Lines To test the potential of a vector in which the coding sequences of both the DTA and TNFα are under the control of the H119 promoter, the present inventors have constructed the pH19-TNF-IRES-DTA vector and used this vector to transfect various cancerous cell lines, as follows.

Experimental Results

The anti-proliferative activity of the pH19-DTA, pH19-TNFα or the pH19-TNF-IRES-DTA expression vectors in various cancerous cell lines—The cytotoxic effect of a vector carrying both the TNFα and DTA coding sequences under the control of the H19 promoter was tested in ovarian, pancreatic carcinoma, bladder, and hepatocellular carcinoma cells. Cells were co-transfected with 2 µg/well of LucSV40 and the indicated concentrations of pH19-DTA, pH19-TNFα or pH19-TNF-IRES-DTA plasmids. Luciferase activity was determined and compared to that of cells transfected with LucSV40 alone. As is shown in FIGS. 5a-i, the killing effect of the plasmid pH19-TNF-IRES-DTA on the carcinoma cells is significantly higher than that showed by the pH19-DTA or the pH19-TNFα vectors alone. DTA and TNF resistant ovarian cells (SK-OV3; 4) were efficiently killed using the pH19-TNF-IRES-DTA plasmid while no cytotoxic effect was detected using the DTA-$H_{19}$ plasmid alone.

Figure 6A:
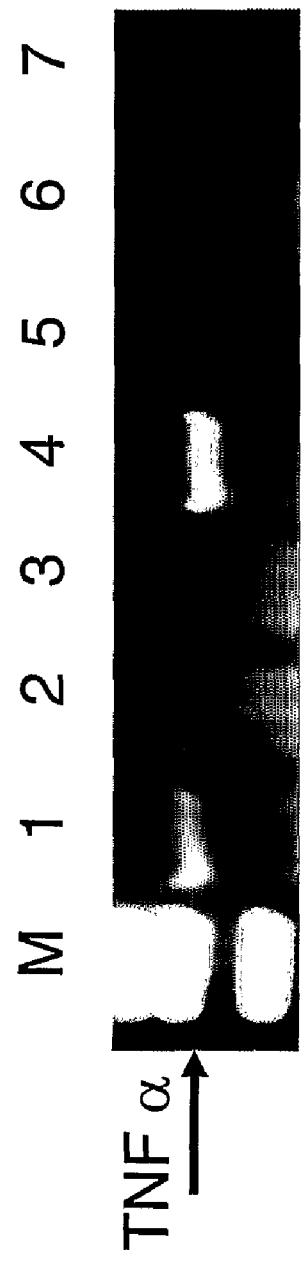
FIGS. 6a-b are RT-PCR analyses depicting the level of TNFα transcripts in RNA isolated from SK-OV3 cells transfected with the pH19-TNFα or with the pH19-TNF-IRES-DTA plasmids, or from SK-OV3 cells which were grown in the presence of the TNFα protein in the culture medium.
Figure 6B:
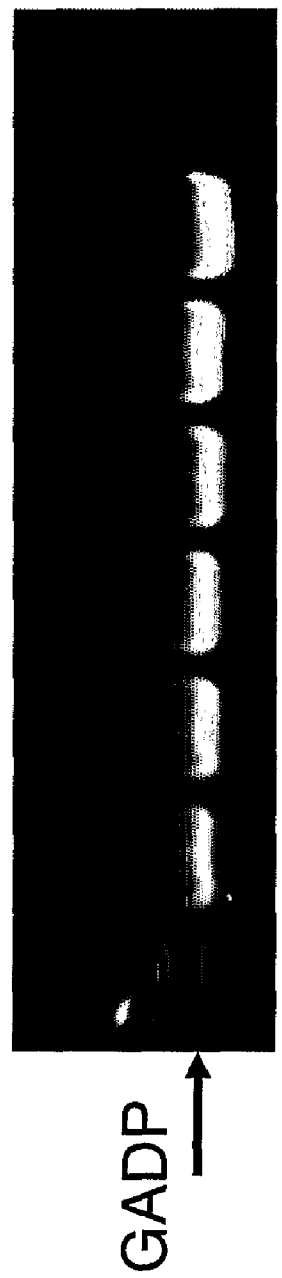

In-vitro expression of the TNFα mRNA—The TNFα mRNA levels were determined by RT-PCR in the SK-OV3 cell line (which is DTA and TNF resistance) following transfection with 0.02 µg/well of the pH19-TNFα or the pH19-TNF-IRES-DTA expression vectors or the addition of 10 ng/ml or 100 ng/ml of the TNFα protein to the culture medium. 48 hours after transfection or the addition of the TNF protein into the culture medium, the total RNA was extracted from the cells. As is shown in FIGS. 6a-b, the TNFα transcript is present in the cells transfected with a control plasmid (LucSV40) and in the untreated cells (lanes 1, 6). Higher levels of TNFα transcript were detected in the cells transfected with the pH 19-TNF-IRES-DTA vector (lane 4) as compared with cells transfected with the pH19-TNFα vector (lane 2). In addition, a decrease in the TNFα RNA levels is seen in cells treated with 100 ng/ml of the TNFα protein (lane 5) as compared with that determined in cells treated with 10 ng/ml of the TNFα protein (lane 3).

Altogether, these results demonstrate that expression of both the TNFα and the DTA coding sequences under the transcriptional control of the H19 promoter is highly efficient in suppressing the growth of a wide variety of cancerous cells, including cell lines which are known to be resistance to both DTA and TNF treatment. In addition, the results demonstrate that the intracellular level of TNFα is higher in cells transfected with the pH19-TNF-IRES-DTA vector than in cells transfected with the pH19-TNFα vector or in cells which are grown in the presence of exogenous TNFα protein provided in the culture medium.

Example 3

The pH19-TNF-IRES-DTA Vector is Suitable for In Vivo Treatment of Cancer

To further test the capacity of the pH19-TNF-IRES-DTA vector to treat cancer, subcutaneous tumors were injected with the various H19-regulated expression construct, as follows.

Experimental Results

Figure 7A:
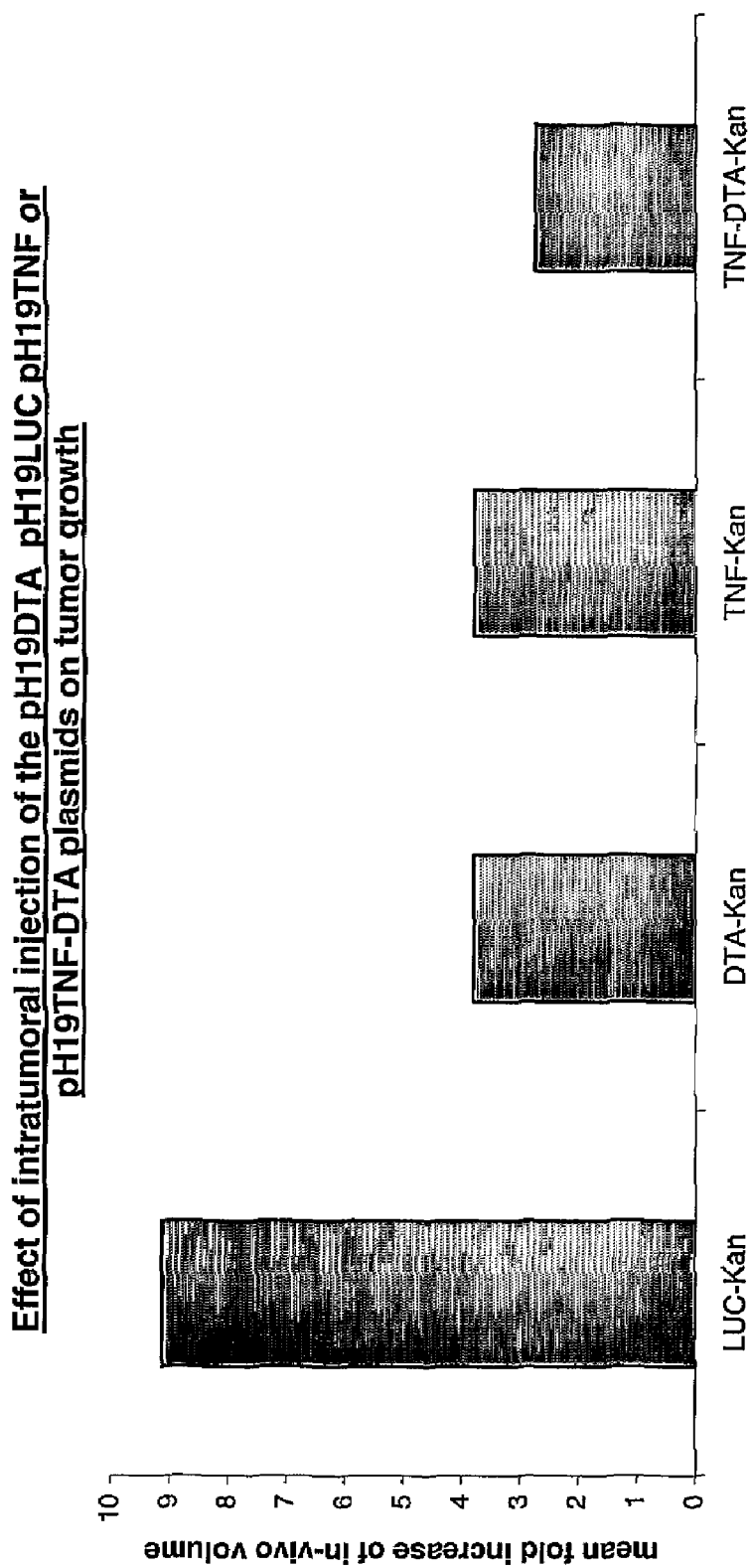
FIGS. 7a-b are histograms depicting the effect of direct intratumoral injection of the pH19-DTA, pH19-TNFα or the pH19-TNF-IRES-DTA vector on the growth of subcutaneous ovarian tumors in nude mice. Mice received 4 injections of 25 μg of pH19-TNF-IRES-DTA (TNF-DTA-Kan), pH19-TNFα (TNF-Kan), pH19-DTA (DTA-Kan) or pH19-Luc complexed with PEI (LUC-Kan) within two days intervals. One day after the last treatment animals were sacrificed. Tumor dimensions were measured in situ prior to the treatment with the plasmid and after sacrifice.
Figure 7B:
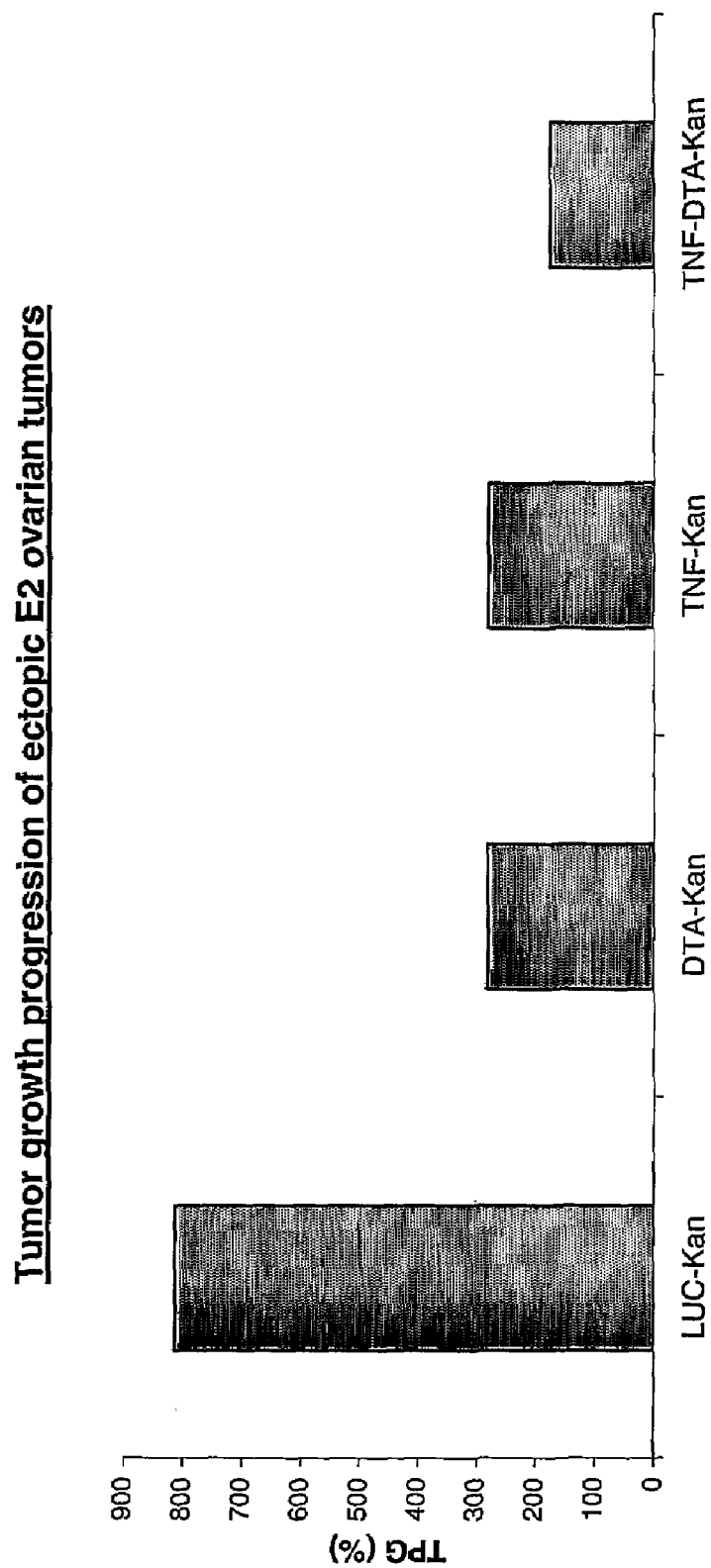

Treatment of heterotopic subcutaneous tumors—The ability of the pH19-TNF-IRES-DTA, pH19-TNFα or pH19-DTA vectors to promote cancer cell killing and inhibit tumor growth in-vivo was analyzed. ES-2 human ovarian cancer cells were subcutaneously injected into the back of 6-7 weeks old Athymic female mice in order to develop a model for heterotopic ovarian cancer. 10 days after the subcutaneous cell inoculation, the mice developed measurable heterotopic tumors. The therapeutic potential of the pH19-TNF-IRES-DTA, pH19-TNFα or pH19-DTA vectors was tested by directly injecting the expression vectors into the developed ovarian cancer tumors. Briefly, tumors of each group of mice were directly injected with 25 µg/tumor of the pH19-TNF-IRES-DTA, pH19-TNFα or pH19-DTA vectors and the tumors of the control group were treated with 25 µg/tumor of pH19-Luc vector. The size of the tumors was determined and in-vivo fold increase of the tumor size was calculated at the end of each treatment. As is shown in FIGS. 7a-b, four injections of the pH19-TNF-IRES-DTA, pH19-TNFα or pH19-DTA vectors were able to inhibit the tumor development by 55%, 41% and 32%, respectively, compared to four injections of the reporter vector pH19-Luc. The tumor growth inhibition of the pH19-TNF-IRES-DTA treated tumors, showed an additive effect as compared to pH 19-TNFα or pH19-DTA treated tumors, rather than synergistically as observed in vitro (see FIGS. 5a-i).

Altogether, these results demonstrate that the H19-driven expression of TNFα and/or DTA can be used to treat established tumors such as ovarian cancer tumors.

Analysis and Discussion

TNFα and DTA trigger DNA fragmentation and target cell lysis with similar kinetics. Protein synthesis inhibition by DTA is not sufficient to target cell lysis. Based on these similarities, DTA and TNFα may either share a common cytolytic pathway or may overlap in their cytolytic pathway.

The results presented here demonstrate that, when used in combination, the DTA and the human TNFα act synergistically in their cytotoxic activity against human ovarian, pancreatic, bladder, and hepatocellular carcinoma cell lines. The cytotoxic activity was observed in both sensitive and resistant cells.

Thus, transfection of cells with the pH19-TNF-IRES-DTA construct resulted in enhanced cytotoxicity. The DTA and TNF resistant ovarian cells, SK-OV3, are efficiently killed using the H19-TNF-IRES-DTA plasmid while no cytotoxic effect is detected using the pH19-DTA plasmid. This may become important in tumors which are resistant to a variety of drugs including DTA or TNF.

The in-vivo experiments shown in FIGS. 7a-b demonstrate that administration of the pH19-TNF-IRES-DTA construct in a heterotopic mouse model results in an additive effect (as compared to the use of the pH19-TNFα or pH19-DTA vectors) and not a synergistic effect as indicated in the in vitro experiments. These results are probably due to the cytotoxic effect shown by the pH19-TNFα alone in the animal model which was not detected in cell lines.

These results are supported by additional results in which using the DTA and the TNF proteins in combination against human ovarian or renal cell carcinoma cell lines, resulted in synergistic cytotoxic activity (4, 30).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES

Additional References Cited in Text

1. Niel H B, Maucer A M et al. 1994 cytotoxic effects of alpha- and gamma-interferon and tumor necrosis factor in human bladder tumor cell lines Urol Res 22: 247-250
2. Glazier D B, Balinson R R, et al 1995 Intravesical recombinant tumor necrosis factor in the treatment of superficial bladder cancer: an Eastern cooperative Oncology Group study J Urol 154:66-68
3. Horiguchi Y, Larchian W A et al 2000 Intravesical liposome-mediated interleukin-2 gene therapy in orthotopic murine bladder cancer model Gene Ther 7: 844-851
4. Morimoto H, Safrit J, and Bonavida B 1991 Synergistic effects of tumor necrosis factor-α and diphtheria toxin-mediated cytotoxicity in sensitive and resistant human ovarian tumor cell lines. J. Immunol. 147: 2609-2616
5. Adriaenssens E, Lottin S, Berteaux N, Hornez L, Fauquette W, Fafeur V, Peyrat J P, Le Bourhis X, Hondermarck H, Coll J, Dugimont T and Curgy J J (2002) Cross-talk between mesenchyme and epithelium increases H19 gene expression during scattering and morphogenesis of epithelial cells. Exp Cell Res 275, 215-229.
6. Ariel 1, Ayesh S, Gofrit O, Ayesh B, Abdul-Ghani R, Pizov G, Smith Y, Sidi A, Birman T, Schneider T, de-Groot N and Hochberg A (2004) Gene expression in the bladder carcinoma rat model. Mol Carcinog 41, 69-76.
7. Ariel I, Lustig O, Oyer C E, Elkim M, Gonik B, Rachmilewitz J, Biran H, Goshen R, de Groot N and Hochberg A (1994) Relaxation of imprinting in trophoblastic disease. Gynecol Oncol 53, 212-219.
8. Ayesh B, Matouk I, Ohana P, Sughayer M A, Birman T, Ayesh S, Schneider T, de Groot N and Hochberg A (2003) Inhibition of tumor growth by DTA expressed under the control of IGF2 P3 and P4 promoter sequences. Mol Ther 7, 535-541.
9. Ayesh S, Matouk 1, Schneider T, Ohana P, Laster M, Al-Sharef W, de-Groot N and Hochberg A (2002) Possible physiological role of H19 RNA. Mol Carcinog 35, 63-74.
10. Bartolomei M S, Zemel S and Tilghman S M (1991) Parental imprinting of the mouse H19 gene. Nature 351, 153-155.
11. Brannan C I, Dees E C, Ingram R S and Tilghman S M (1990) The product of the H19 gene may function as an RNA. Mol Cell biol 10, 28-36.
12. Elkin M, Ayesh S, Schneider T, de Groot N, Hochberg A and Ariel I (1998) The dynamics of the imprinted H19 gene expression in the mouse model of bladder carcinoma induced by N-Butyl-N-(4-hydroxybutyl)nitrosamine. Carcinogenesis 19, 2095-2099.
13. Elkin M, Shevelev A, Schulze E, Tyckocinsky M, Cooper M, Ariel I, Pode D, Kopf N, de Groot N and Hochberg A (1995) The expression of the H19 and IGF-2 genes in human bladder carcinoma. FEBS Lett 374, 57-61.

14. Folkman J and Kalluri R (2004) cancer without disease. Nature 427, 787.
15. Graveel C R, Jatkoe T, Madore S J, Holt A L and Farnham P J (2001) Expression profiling and identification of novel genes in hepatocellular carcinomas. Oncogene 20, 2704-2712.
16. Kaplan R, Luettich K, Heguy A, Hackett N R, Harvey B G and Crystal R G (2003) Monoallelic up-regulation of the imprinted H19 gene in airway epithelium of phenotypically normal cigarette smokers. Cancer Res 63, 1475-1482.
17. Leibovitch M P, Nguyen V C, Gross M S, Solhonne B, Leibovitch S A and Bernheim A (1991) The human ASM (adult skeletal muscle) gene: expression and chromosomal assignment to 11p15. Biochem Biophys Res Commun 180, 1241-1250.
18. Lottin S, Adriaenssens E, Dupressoir T, Berteaux N, Montpellier C, Coll J, Dugimont T and Curgy J J (2002) Overexpression of an ectopic H19 gene enhances the tumorigenic properties of breast cancer cells. Carcinogesis 23, 1885-1895.
19. Lottin S, Vercoutter-Edouart A S, Adriaenssens E, Czeszak X, Lemoine J, Roudbaraki M, Coll J, Hondermarck H, Dugimont T and Curgy J J (2002) Thioredoxin post-transcriptional regulation by H19 provides a new function to mRNA-like non-coding RNA. Oncogene 21, 1625-1631.
20. Lustig-Yariv O, Schulze E, Komitowski D, Erdmann V, Schneider T, de Groot N and Hochberg A (1997) The expression of the imprinted genes H19 and IGF-2 in choriocarcinoma cell lines. Is H119 a tumor suppressor gene? Oncogene 15, 169-177.
21. Matouk I, Ayesh B, Schneider T, Ayesh S, Ohana P, de-Groot N, Hochberg A and Galun E (2004) Oncofetal splice pattern the human H19 gene. Biochem Biophys Res Commun 318, 916-919.
22. Matouk I, Ohana P, Ayesh S, Sidi A, Czerniak A, de-Groot N and Hochberg A (2005) The oncofetal H19 RNA in human cancer, from the bench to the patient. Gene Ther Mol Biol (In press).
23. Ohana P, Gofrit 0, Ayesh S, Al-sharef W, Mizrahi A, Birman T, Schneider T, Matouk I, de-Groot N, Tavdy E, Sidi A A and Hochberg A (2004) Regulatory sequences of the H19 gene in DNA based therapy of bladder cancer. Gene Ther Mol Biol 8, 181-192.
24. Rachmilewitz J, Elkim M, Rosensaft J, Gelman-Kohan Z, Ariel I, Lustig O, Schneider T, Goshen R, Biran H, de Groot N and Hochberg A (1995) H19 expression and tumorigenicity of choriocarcinoma derived cell lines. Oncogene 11, 863-870.
25. Rachmilewitz J, Goshen R, Ariel I, Schneider T, de Groot N and Hochberg A (1992b) Parental imprinting of the human H19 gene. FEBS Lett 309, 25-28.
26. Rodesch F, Simon P, Donner C and Jauniaux E (1991) Oxygen measurements in endometrial and trophoblastic tissues during early pregnancy. Obstet Gynecol 80, 283-285.
27. Stuhlmuller B, Kunisch E, Franz J, Martinez-Gamboa L, Hernandez M M, Pruss A, Ulbrish N, Erdmamn V A, Burmester G R and Kinne R W (2003) Detection of oncofetal h19 RNA in rheumatoid arthritis synovial tissue. Am J Pathol 163, 901-911.
28. Venables J P (2004) Abberant and alternative splicing in cancer. Cancer Res 64, 2647-2654.
29. Zhang Y and Tycko B (1992) Monoallelic expression of the human H19 gene. Nat Genet 1, 40-44.
30. Morimoto H, Bonavida B. Diphtheria toxin- and Pseudomonas A toxin-mediated apoptosis. ADP ribosylation of elongation factor-2 is required for DNA fragmentation and cell lysis and synergy with tumor necrosis factor-alpha. J. Immunol. 1992, 149: 2089-94.
31. Mizutani Y, Bonavida B, Yoshida O. Cytotoxic effect of diphtheria toxin used alone or in combination with other agents on human renal cell carcinoma cell lines. 1994, Urol Res. 22:261-6.

What is claimed is:

1. A nucleic acid construct comprising:
   (i) a first nucleic acid sequence encoding tumor necrosis factor alpha (TNF alpha);
   (ii) a second nucleic acid sequence encoding a Diphtheria toxin; and
   (iii) at least one additional nucleic acid sequence comprising a cancer specific promoter; said TNF alpha and Diphtheria toxin encoding sequences being under expression control of said cancer specific promoter,
   wherein the first nucleic acid sequence and the second nucleic acid sequence are transcriptionally linked via an internal ribosome entry site (IRES) linker nucleic acid sequence, and wherein said construct provides enhanced intracellular levels of TNF alpha compared to cells transfected with a nucleic acid sequence encoding only TNF alpha.

2. The nucleic acid construct of claim 1, wherein said TNF alpha is a secreted TNF alpha.

3. The nucleic acid construct of claim 1, wherein said TNF alpha is a non-secreted TNF alpha.

4. The nucleic acid construct of claim 1, wherein said cancer-specific promoter is selected from the group consisting of IGF-1, IGF-2 P3 and IGF-2 P4 promoters.

5. The nucleic acid construct of claim 1, wherein said cancer-specific promoter is an H19 promoter.

6. A nucleic acid construct having the nucleic acid sequence as set forth in SEQ ID NO:13.

7. A pharmaceutical composition comprising, as an active ingredient a nucleic acid construct according to claim 1 and a pharmaceutically acceptable carrier or diluent.

8. The pharmaceutical composition of claim 7 further comprising a transfection agent.

* * * * *

SEQUENCE LISTING

<160> NUMBER OF SEQ ID NOS: 22

<210> SEQ ID NO 1
<211> LENGTH: 591
<212> TYPE: DNA
<213> ORGANISM: Artificial sequence
<220> FEATURE:
<223> OTHER INFORMATION: diphtheria A chain toxin (DTA) coding sequnce

<400> SEQUENCE: 1

```
atggatcctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaaccgc tctctggaaa agctggaggc     240
gtggtcaaag tgacgtatcc aggactgacg aaggttctcg cactaaaagt ggataatgcc     300
gaaactatta agaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtgaaaaac gtggccaaga tgcgatgtat     540
gagtatatgg ctcaagcctg tgcaggaaat cgtgtcaggc gatctttgtg a               591
```

<210> SEQ ID NO 2
<211> LENGTH: 196
<212> TYPE: PRT
<213> ORGANISM: Artificial sequence
<220> FEATURE:
<223> OTHER INFORMATION: diphtheria A chain toxin (DTA)

<400> SEQUENCE: 2

```
Met Asp Pro Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Leu
        195
```

<210> SEQ ID NO 3
<211> LENGTH: 831
<212> TYPE: DNA
<213> ORGANISM: Artificial sequence
<220> FEATURE:
<223> OTHER INFORMATION: H19 promoter

<400> SEQUENCE: 3

```
gacaaccctc accaagggcc aaggtggtga ccgacggacc cacagcgggg tggctggggg     60
agtcgaaact cgccagtctc cactccactc ccaaccgtgg tgccccacgc gggcctggga    120
gagtctgtga ggccgcccac cgcttgtcag tagagtgcgc ccgcgagccg taagcacagc    180
ccggcaacat gcggtcttca gacaggaaag tggccgcgaa tgggaccggg gtgcccagcg    240
gctgtgggga ctctgtcctg cggaaaccgc ggtgacgagc acaagctcgg tcaactggat    300
gggaatcggc ctgggggctc ggcaccgcgc ccaccagggg gtttgcggca cttccctctg    360
cccctcagca ccccacccct actctccagg aacgtgagtt ctgagccgtg atggtggcag    420
gaaggggccc tctgtgccat ccgagtcccc agggacccgc agctggcccc cagccatgtg    480
caaagtatgt gcagggcgct ggcaggcagg gagcagcagg catggtgtcc cctgagggga    540
gacagtggtc tgggagggag aagtcctggc cctgagggag gtgatggggc aatgctcagc    600
```

```
cctgtctccg gatgccaaag gaggggtgcg gggaggccgt ctttggagaa ttccaggatg    660
ggtgctgggt gagagagacg tgtgctggaa ctgtccaggg cggaggtggg ccctgcgggg    720
gccctcggga gggccctgct ctgattggcc ggcagggcag gggcgggaat tctgggcggg    780
gccaccccag ttagaaaaag cccgggctag gaccgaggag cagggtgagg g            831

<210> SEQ ID NO 4
<211> LENGTH: 720
<212> TYPE: DNA
<213> ORGANISM: Artificial sequence
<220> FEATURE:
<223> OTHER INFORMATION: TNF-Alpha coding sequence

<400> SEQUENCE: 4
tcatgagcac cgagagcatg atcagggatg tggagctggc cgaggaggcc ctgcccaaga     60
aaacaggcgg ccctcagggc agcagaagat gcctgttcct gagcctgttc agcttcctga    120
tcgtggccgg agccaccacc ctgttctgcc tgctgaactt cggcgtgatc ggccccccaga   180 gagaggagtt ccccagagac ctgagcctga tctccccccct ggcccaggct gtgagaagca   240
gcagcagaac ccccagcgac aagcccgtgg cccacgtggt ggccaacccc caggccgagg    300
gccagctgca gtggctgaac agaagagcca acgccctgct ggccaacggc gtggagctga    360
gagacaacca gctggtggtg cccagcgagg gcctgtacct gatctacagc caggtgctgt    420
tcaagggcca gggctgcccc agcacccacg tgctgctgac ccacaccatc agcagaatcg    480
ccgtgtccta ccagaccaag gtgaacctgc tgtccgccat caagagccct tgccagagag    540
agacccccga gggcgccgag gccaagccct ggtacgagcc tatctacctg gcggcgtgt    600 tccagctgga aagggcgac agactgagcg ccgagatcaa cagacccgac tacctggatt    660 cgccgagag cggccaggtg tacttcggca tcatcgccct gtgataatct agaaccatgg    720

<210> SEQ ID NO 5
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 5
aaacttgttt attgcagctt ataatg                                          26

<210> SEQ ID NO 6
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 6
gctcaggtct ctggggaact cctctctctg gggggatgga gagcgtatgt tagtac        56

<210> SEQ ID NO 7
<211> LENGTH: 4612
<212> TYPE: DNA
<213> ORGANISM: Artificial sequence
<220> FEATURE:
<223> OTHER INFORMATION: H19-TNFalpha-KANA

<400> SEQUENCE: 7
tctatcgata ggtaccgaca accctcacca agggccaagg tggtgaccga cggacccaca     60
gcggggtggc tgggggagtc gaaactcgcc agtctccact ccactcccaa ccgtggtgcc    120
```

-continued

```
ccacgcgggc ctgggagagt ctgtgaggcc gcccaccgct tgtcagtaga gtgcgcccgc    180
gagccgtaag cacagcccgg caacatgcgg tcttcagaca ggaaagtggc cgcgaatggg    240
accggggtgc ccagcggctg tggggactct gtcctgcgga aaccgcggtg acgagcacaa    300
gctcggtcaa ctggatggga atcggcctgg ggggctggca ccgcgcccac caggggcttt    360
gcggcacttc cctctgcccc tcagcacccc acccctactc tccaggaacg tgagttctga    420
gccgtgatgg tggcaggaag gggccctctg tgccatccga gtccccaggg acccgcagct    480
ggcccccagc catgtgcaaa gtatgtgcag ggcgctggca ggcagggagc agcaggcatg    540
gtgtccctg  aggggagaca gtggtctggg agggagaagt cctggaccct gagggaggtg    600
atggggcaat gctcagccct gtctccggat gccaaaggag gggtgcgggg aggccgtctt    660
tggagaattc caggatgggt gctggtgag  agagacgtgt gctggaactg tccagggcgg    720
aggtgggccc tgcgggggcc ctcgggaggg ccctgctctg attggccggc agggcagggg    780
cgggaatcct gggcggggcc accccagtta gaaaaagccc gggctaggac cgaggagcag    840
ggtgagggag aagcttggca ttccggtact gttggtaaag ccaccatgag caccgagagc    900
atgatcaggg atgtggagct ggccgaggag gccctgccca agaaaacagg cggccctcag    960
ggcagcagaa gatgcctgtt cctgagcctg ttcagcttcc tgatcgtggc cggagccacc   1020
accctgttct gcctgctgaa cttcggcgtg atcggccccc agagagagga gttccccaga   1080
gacctgagcc tgatctcccc cctggcccag gctgtgagaa gcagcagcag aacccccagc   1140
gacaagcccg tggcccacgt ggtggccaac ccccaggccg agggccagct gcagtggctg   1200
aacagaagag ccaacgccct gctggccaac ggcgtggagc tgagagacaa ccagctggtg   1260
gtgcccagcg agggcctgta cctgatctac agccaggtgc tgttcaaggg ccagggctgc   1320
cccagcaccc acgtgctgct gacccacacc atcagcagaa tcgccgtgtc ctaccagacc   1380
aaggtgaacc tgctgtccgc catcaagagc ccttgccaga gagagacccc cgagggcgcc   1440
gaggccaagc cctggtacga gcctatctac ctgggcggcg tgttccagct ggagaagggc   1500
gacagactga cgccgagat  caacagaccc gactacctgg atttcgccga gagcggccag   1560
gtgtacttcg gcatcatcgc cctgtgataa tctagagtcg gggcggccgg ccgcttcgag   1620
cagacatgat aagatacatt gatgagtttg gacaaaccac aactagaatg cagtgaaaaa   1680
aatgctttat ttgtgaaatt tgtgatgcta ttgctttatt tgtaaccatt ataagctgca   1740
ataaacaagt taacaacaac aattgcattc attttatgtt tcaggttcag ggggaggtgt   1800
gggaggtttt ttaaagcaag taaaacctct acaaatgtgg taaaatcgat aaggatccgt   1860
cgaccgatgc ccttgagagc cttcaaccca gtcagctcct tccggtgggc gcggggcatg   1920
actatcgtcg ccgcacttat gactgtcttc tttatcatgc aactcgtagg acaggtgccg   1980
gcagcgctct tccgcttcct cgctcactga ctcgctgcgc tcggtcgttc ggctgcggcg   2040
agcggtatca gctcactcaa aggcggtaat acgttatcc  acagaatcag ggataacgc    2100
aggaaagaac atgtgagcaa aaggccagca aaaggccagg aaccgtaaaa aggccgcgtt   2160
gctggcgttt ttccataggc tccgcccccc tgacgagcat cacaaaaatc gacgctcaag   2220
tcagaggtgg cgaaacccga caggactata aagataccag gcgtttcccc ctggaagctc   2280
cctcgtgcgc tctcctgttc cgaccctgcc gcttaccgga tacctgtccg cctttctccc   2340
ttcgggaagc gtggcgcttt ctcatagctc acgctgtagg tatctcagtt cggtgtaggt   2400
cgttcgctcc aagctgggct gtgtgcacga accccccgtt cagcccgacc gctgcgcctt   2460
atccggtaac tatcgtcttg agtccaaccc ggtaagacac gacttatcgc cactggcagc   2520
```

-continued

| | |
|---|---|
| agccactggt aacaggatta gcagagcgag gtatgtaggc ggtgctacag agttcttgaa | 2580 |
| gtggtggcct aactacggct acactagaag aacagtattt ggtatctgcg ctctgctgaa | 2640 |
| gccagttacc ttcggaaaaa gagttggtag ctcttgatcc ggcaaacaaa ccaccgctgg | 2700 |
| tagcggtggt ttttttgttt gcaagcagca gattacgcgc agaaaaaaag gatctcaaga | 2760 |
| agatcctttg atcttttcta cggggtctga cgctcagtgg aacgaaaact cacgttaagg | 2820 |
| gattttggtc atgagattat caaaaaggat cttcacctag atccttttaa attaaaaatg | 2880 |
| aagttttaaa tcaatctaaa gtatatatga gtaaacttgg tctgacagtt agaaaaactc | 2940 |
| atcgagcatc aaatgaaact gcaatttatt catatcagga ttatcaatac catattttg | 3000 |
| aaaaagccgt ttctgtaatg aaggagaaaa ctcaccgagg cagttccata ggatggcaag | 3060 |
| atcctggtat cggtctgcga ttccgactcg tccaacatca atacaaccta ttaatttccc | 3120 |
| ctcgtcaaaa ataaggttat caagtgagaa atcaccatga gtgacgactg aatccggtga | 3180 |
| gaatggcaaa agtttatgca tttctttcca gacttgttca acaggccagc cattacgctc | 3240 |
| gtcatcaaaa tcactcgcat caaccaaacc gttattcatt cgtgattgcg cctgagcgag | 3300 |
| acgaaatacg cgatcgctgt taaaaggaca attacaaaca ggaatcgaat gcaaccggcg | 3360 |
| caggaacact gccagcgcat caacaatatt ttcacctgaa tcaggatatt cttctaatac | 3420 |
| ctggaatgct gttttcccgg ggatcgcagt ggtgagtaac catgcatcat caggagtacg | 3480 |
| gataaaatgc ttgatggtcg gaagaggcat aaattccgtc agccagttta gtctgaccat | 3540 |
| ctcatctgta acatcattgg caacgctacc tttgccatgt ttcagaaaca actctggcgc | 3600 |
| atcgggcttc ccatacaatc gatagattgt cgcacctgat tgcccgacat tatcgcgagc | 3660 |
| ccatttatac ccatataaat cagcatccat gttggaattt aatcgcggcc tagagcaaga | 3720 |
| cgtttcccgt tgaatatggc tcatactctt ccttttcaa tattattgaa gcatttatca | 3780 |
| gggttattgt ctcatgagcg gatacatatt tgaatgtatt tagaaaaata acaaataggg | 3840 |
| ggttccgcgc acatttcccc gaaaagtgcc acctgacgcg ccctgtagcg gcgcattaag | 3900 |
| cgcggcgggt gtggtggtta cgcgcagcgt gaccgctaca cttgccagcg ccctagcgcc | 3960 |
| cgctcctttc gctttcttcc cttcctttct cgccacgttc gccggctttc cccgtcaagc | 4020 |
| tctaaatcgg gggctccctt tagggttccg atttagtgct ttacggcacc tcgaccccaa | 4080 |
| aaaacttgat tagggtgatg gttcacgtag tgggccatcg ccctgataga cggttttcg | 4140 |
| ccctttgacg ttggagtcca cgttctttaa tagtggactc ttgttccaaa ctggaacaac | 4200 |
| actcaaccct atctcggtct attcttttga tttataaggg attttgccga tttcggccta | 4260 |
| ttggttaaaa aatgagctga tttaacaaaa atttaacgcg aattttaaca aaatattaac | 4320 |
| gcttacaatt tgccattcgc cattcaggct gcgcaactgt tgggaagggc gatcggtgcg | 4380 |
| ggcctcttcg ctattacgcc agcccaagct accatgataa gtaagtaata ttaaggtacg | 4440 |
| ggaggtactt ggagcggccg caataaaata tctttatttt cattacatct gtgtgttggt | 4500 |
| ttttgtgtg aatcgatagt actaacatac gctctccatc aaaacaaaac gaaacaaaac | 4560 |
| aaactagcaa aataggctgt ccccagtgca agtgcaggtg ccagaacatt tc | 4612 |

<210> SEQ ID NO 8
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 8

-continued

```
ttaaccatgg cccctctccc tccc                                           24
```

<210> SEQ ID NO 9
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 9

```
ttaatcatga tgtggccata ttatcatcgt                                     30
```

<210> SEQ ID NO 10
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 10

```
gaaaaagccc gggctag                                                   17
```

<210> SEQ ID NO 11
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 11

```
cccgtggtac gaagaaaag                                                 19
```

<210> SEQ ID NO 12
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 12

```
gacaaacgca caccggc                                                   17
```

<210> SEQ ID NO 13
<211> LENGTH: 5864
<212> TYPE: DNA
<213> ORGANISM: Artificial sequence
<220> FEATURE:
<223> OTHER INFORMATION: pH19-TNFalpha-IRES-DTA-KANA

<400> SEQUENCE: 13

```
tctatcgata ggtaccgaca accctcacca agggccaagg tggtgaccga cggacccaca    60
gcggggtggc tgggggagtc gaaactcgcc agtctccact ccactcccaa ccgtggtgcc   120
ccacgcgggc tgggagagt ctgtgaggcc gccaccgct tgtcagtaga gtgcgcccgc    180
gagccgtaag cacagcccgg caacatgcgg tcttcagaca ggaaagtggc cgcgaatggg   240
accggggtgc ccagcggctg tggggactct gtcctgcgga aaccgcggtg acagagcacaa  300
gctcggtcaa ctggatggga atcggcctgg ggggctggca ccgcgcccac caggggggttt   360
gcggcacttc cctctgcccc tcagcacccc acccctactc tccaggaacg tgagttctga   420
gccgtgatgg tggcaggaag gggccctctg tgccatccga gtcccaggg accgcagct    480
ggcccccagc catgtgcaaa gtatgtgcag ggcgctggca ggcagggagc agcaggcatg    540
gtgtcccctg aggggagaca gtggtctggg agggagaagt cctggaccct gagggaggtg   600
```

```
atggggcaat gctcagccct gtctccggat gccaaaggag gggtgcgggg aggccgtctt      660
tggagaattc caggatgggt gctggtgag  agagacgtgt gctggaactg tccagggcgg      720
aggtgggccc tgcgggggcc ctcgggaggg ccctgctctg attggccggc agggcagggg      780
cgggaatcct gggcgggccc accccagtta gaaaaagccc gggctaggac cgaggagcag      840
ggtgagggag aagcttggca ttccggtact gttggtaaag ccaccatgag caccgagagc      900
atgatcaggg atgtggagct ggccgaggag gccctgccca agaaaacagg cggccctcag      960
ggcagcagaa gatgcctgtt cctgagcctg ttcagcttcc tgatcgtggc cggagccacc     1020
accctgttct gcctgctgaa cttcggcgtg atcggccccc agagagagga gttccccaga     1080
gacctgagcc tgatctcccc cctggcccag gctgtgagaa gcagcagcag aaccccagc     1140 gacaagcccg tgcccacgt  ggtggccaac cccaggccg  agggcagct  gcagtggctg     1200 aacagaagag ccaacgccct gctggccaac ggcgtggagc tgagagacaa ccagctggtg     1260
gtgcccagcg agggcctgta cctgatctac agccaggtgc tgttcaaggg ccagggctgc     1320
cccagcaccc acgtgctgct gacccacacc atcagcagaa tcgccgtgtc ctaccagacc     1380
aaggtgaacc tgctgtccgc catcaagagc ccttgccaga gagagacccc cgagggcgcc     1440
gaggccaagc cctggtacga gcctatctac ctgggcggcg tgttccagct ggagaagggc     1500
gacagactga gcgccgagat caacagaccc gactacctgg atttcgccga gagcggccag     1560
gtgtacttcg gcatcatcgc cctgtgataa tctagaacca tggcccctct ccctcccccc     1620
cccctaacgt tactgccga  agccgcttgg aataaggccg gtgtgcgttt gtctatatgt     1680
tattttccac catattgccg tcttttggca atgtgagggc ccggaaacct ggccctgtct     1740
tcttgacgag cattcctagg ggtctttccc ctctcgccaa aggaatgcaa ggtctgttga     1800
atgtcgtgaa ggaagcagtt cctctggaag cttcttgaag acaaacaacg tctgtagcga     1860
ccctttgcag gcagcggaac cccccacctg gcgacaggtg cctctgcggc caaaagccac     1920
gtgtataaga tacacctgca aaggcggcac aaccccagtg ccacgttgtg agttggatag     1980
ttgtggaaag agtcaaatgg ctctcctcaa gcgtattcaa caaggggctg aaggatgccc     2040
agaaggtacc ccattgtatg ggatctgatc tggggcctcg gtacacatgc tttacatgtg     2100
tttagtcgag gttaaaaaaa cgtctaggcc ccccgaacca cggggacgtg gttttccttt     2160
gaaaaacacg atgataatat ggccacatca tggatcctga tgatgttgtt gattcttcta     2220
aatcttttgt gatggaaaac ttttcttcgt accacgggac taaacctggt tatgtagatt     2280
ccattcaaaa aggtatacaa aagccaaaat ctggtacaca aggaaattat gacgatgatt     2340
ggaaagggtt ttatagtacc gacaataaat acgacgctgc gggatactct gtagataatg     2400
aaaacccgct ctctggaaaa gctggaggcg tggtcaaagt gacgtatcca ggactgacga     2460
aggttctcgc actaaaagtg gataatgccg aaactattaa gaaagagtta ggtttaagtc     2520
tcactgaacc gttgatggag caagtcggaa cggaagagtt tatcaaaagg ttcggtgatg     2580
gtgcttcgcg tgtagtgctc agccttccct tcgctgaggg gagttctagc gttgaatata     2640
ttaataactg gaacaggcg  aaagcgttaa gcgtagaact tgagattaat tttgaaaccc     2700
gtggaaaacg tggccaagat gcgatgtatg agtatatggc tcaagcctgt gcaggaaatc     2760
gtgtcaggcg atctttgtga aggaacctta cttctgtggt gtgacataat tggacaaact     2820
acctacagag atttggggat cctctagagt cggggcggcc ggccgcttcg agcagacatg     2880
ataagataca ttgatgagtt tggacaaacc acaactagaa tgcagtgaaa aaaatgcttt     2940
atttgtgaaa tttgtgatgc tattgcttta tttgtaacca ttataagctg caataaacaa     3000
```

```
gttaacaaca acaattgcat tcattttatg tttcaggttc aggggaggt gtgggaggtt    3060
ttttaaagca agtaaaacct ctacaaatgt ggtaaaatcg ataaggatcc gtcgaccgat    3120
gcccttgaga gccttcaacc cagtcagctc cttccggtgg gcgcggggca tgactatcgt    3180
cgccgcactt atgactgtct tctttatcat gcaactcgta ggacaggtgc cggcagcgct    3240
cttccgcttc ctcgctcact gactcgctgc gctcggtcgt tcggctgcgg cgagcggtat    3300
cagctcactc aaaggcggta atacggttat ccacagaatc aggggataac gcaggaaaga    3360
acatgtgagc aaaaggccag caaaaggcca ggaaccgtaa aaaggccgcg ttgctggcgt    3420
ttttccatag gctccgcccc cctgacgagc atcacaaaaa tcgacgctca agtcagaggt    3480
ggcgaaaccc gacaggacta taaagatacc aggcgtttcc ccctggaagc tccctcgtgc    3540
gctctcctgt tccgaccctg ccgcttaccg gatacctgtc cgcctttctc ccttcgggaa    3600
gcgtggcgct ttctcatagc tcacgctgta ggtatctcag ttcggtgtag gtcgttcgct    3660
ccaagctggg ctgtgtgcac gaaccccccg ttcagcccga ccgctgcgcc ttatccggta    3720
actatcgtct tgagtccaac ccggtaagac acgacttatc gccactggca gcagccactg    3780
gtaacaggat tagcagagcg aggtatgtag gcggtgctac agagttcttg aagtggtggc    3840
ctaactacgg ctacactaga agaacagtat ttggtatctg cgctctgctg aagccagtta    3900
ccttcggaaa aagagttggt agctcttgat ccggcaaaca aaccaccgct ggtagcggtg    3960
gtttttttgt ttgcaagcag cagattacgc gcagaaaaaa aggatctcaa gaagatcctt    4020
tgatcttttc tacggggtct gacgctcagt ggaacgaaaa ctcacgttaa gggattttgg    4080
tcatgagatt atcaaaaagg atcttcacct agatcctttt aaattaaaaa tgaagtttta    4140
aatcaatcta agtatatat gagtaaactt ggtctgacag ttagaaaaac tcatcgagca    4200
tcaaatgaaa ctgcaattta ttcatatcag gattatcaat accatatttt tgaaaaagcc    4260
gtttctgtaa tgaaggagaa aactcaccga ggcagttcca taggatggca agatcctggt    4320
atcggtctgc gattccgact cgtccaacat caatacaacc tattaatttc ccctcgtcaa    4380
aaataaggtt atcaagtgag aaatcaccat gagtgacgac tgaatccggt gagaatggca    4440
aaagtttatg catttctttc cagacttgtt caacaggcca gccattacgc tcgtcatcaa    4500
aatcactcgc atcaaccaaa ccgttattca ttcgtgattg cgcctgagcg agacgaaata    4560
cgcgatcgct gttaaaagga caattacaaa caggaatcga atgcaaccgg cgcaggaaca    4620
ctgccagcgc atcaacaata ttttcacctg aatcaggata ttcttctaat acctggaatg    4680
ctgtttcccc ggggatcgca gtggtgagta accatgcatc atcaggagta cggataaaat    4740
gcttgatggt cggaagaggc ataaattccg tcagccagtt tagtctgacc atctcatctg    4800
taacatcatt ggcaacgcta cctttgccat gtttcagaaa caactctggc gcatcgggct    4860
tcccatacaa tcgatagatt gtcgcacctg attgcccgac attatcgcga gcccatttat    4920
acccatataa atcagcatcc atgttggaat ttaatcgcgg cctagagcaa gacgtttccc    4980
gttgaatatg gctcatactc ttccttttc aatattattg aagcatttat cagggttatt    5040
gtctcatgag cggatacata tttgaatgta tttagaaaaa taaacaaata ggggttccgc    5100
gcacatttcc ccgaaaagtg ccacctgacg cgccctgtag cggcgcatta agcgcggcgg    5160
gtgtggtggt tacgcgcagc gtgaccgcta cacttgccag cgccctagcg cccgctcctt    5220
tcgctttctt cccttccttt ctcgccacgt tcgccggctt tccccgtcaa gctctaaatc    5280
gggggctccc tttagggttc cgatttagtg ctttacggca cctcgacccc aaaaaacttg    5340
attagggtga tggttcacgt agtgggccat cgccctgata cggttttt cgccctttga    5400
```

-continued

```
cgttggagtc cacgttcttt aatagtggac tcttgttcca aactggaaca acactcaacc      5460
ctatctcggt ctattctttt gatttataag ggattttgcc gatttcggcc tattggttaa      5520
aaaatgagct gatttaacaa aaatttaacg cgaattttaa caaaatatta acgcttacaa      5580
tttgccattc gccattcagg ctgcgcaact gttgggaagg gcgatcggtg cgggcctctt      5640
cgctattacg ccagcccaag ctaccatgat aagtaagtaa tattaaggta cgggaggtac      5700
ttggagcggc cgcaataaaa tatctttatt ttcattacat ctgtgtgttg gttttttgtg      5760
tgaatcgata gtactaacat acgctctcca tcaaaacaaa acgaaacaaa acaaactagc      5820
aaaataggct gtccccagtg caagtgcagg tgccagaaca tttc                       5864
```

<210> SEQ ID NO 14
<211> LENGTH: 15
<212> TYPE: DNA
<213> ORGANISM: Artificial sequence
<220> FEATURE:
<223> OTHER INFORMATION: Single strand DNA oligonucleotide

<400> SEQUENCE: 14
gccattggcc agggc                                                          15

<210> SEQ ID NO 15
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 15
cgccaccacg ctcttct                                                        17

<210> SEQ ID NO 16
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 16
ggctctccag aacatcatcc ctgc                                                24

<210> SEQ ID NO 17
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 17
gggtgtcgct gttgaagtca gagg                                                24

<210> SEQ ID NO 18
<211> LENGTH: 233
<212> TYPE: PRT
<213> ORGANISM: Artificial sequence
<220> FEATURE:
<223> OTHER INFORMATION: TNF-Alpha

<400> SEQUENCE: 18

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

```
Leu Ser Leu Phe Ser Phe Leu Ile Val Ala Gly Ala Thr Thr Leu Phe
     35                  40                  45

Cys Leu Leu Asn Phe Gly Val Ile Gly Pro Gln Arg Glu Glu Phe Pro
 50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                 85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 19
<211> LENGTH: 833
<212> TYPE: DNA
<213> ORGANISM: Homo sapiens

<400> SEQUENCE: 19
gacaaccctc accaagggcc aaggtggtga ccgacggacc cacagcgggg tggctggggg      60
agtcgaaact cgccagtctc cactccactc ccaaccgtgg tgccccacgc gggcctggga     120
gagtctgtga ggccgcccac cgcttgtcag tagagtgcgc ccgcgagccg taagcacagc     180
ccggcaacat gcggtcttca gacaggaaag tggccgcgaa tgggaccggg gtgcccagcg     240
gctgtgggga ctctgtcctg cggaaaccgc ggtgacgagc acaagctcgg tcaactggat     300
gggaatcggc ctgggggct ggcaccgcgc ccaccagggg gtttgcggca cttccctctg     360
cccctcagca ccccaccct actctccagg aacgtgagtt ctgagccgtg atggtggcag     420
gaaggggccc tctgtgccat ccgagtcccc agggacccgc agctggcccc cagccatgtg     480
caaagtatgt gcagggcgct ggcaggcagg gagcagcagg catggtgtcc cctgagggga     540
gacagtggtc tgggagggag aagtcctggc cctgaggag gtgatgggc aatgctcagc      600 cctgtctccg gatgccaaag gagggtgcg gggaggccgt ctttggagaa ttccaggatg      660
ggtgctgggt gagagagacg tgtgctggaa ctgtccaggg cggaggtggg ccctgcgggg    720
gccctcggga gggccctgct ctgattggcc ggcagggcag gggcgggaat tctgggcggg    780
gccaccccag ttagaaaaag cccgggctag gaccgaggag cagggtgagg gag            833

<210> SEQ ID NO 20
<211> LENGTH: 877
<212> TYPE: DNA
<213> ORGANISM: Artificial sequence
```

```
<220> FEATURE:
<223> OTHER INFORMATION: H19 downstream enhancer region

<400> SEQUENCE: 20
caaggacatg gaatttcgga ccttctgtcc ccaccctctc tgctgagcct aggaacctct      60
gagcagcagg aaggccttgg gtctagagcc tagaaatgga cccccacgtc cacctgccca     120
gcctagaccc ccagcattga agggtggtca gacttcctgt gagaggaagc cactaagcgg     180
gatggacacc atcgcccact ccacccggcc ctgcccagcc ctgcccagtc cagcccagtc     240
cagcccagcc ctgcccttcc cagccctgcc cagcccagct catccctgcc ctacccagcc     300
cagccctgtc ctgccctgcc cagcccagcc cagcccagcc ctgccctgcc ctgccctgcc     360
cttcccagcc ctgaccttcc cagccctgcc cagcccagct catccctgcc ctacccagct     420
cagccctgcc ctgccctgcc ctgccctgcc cagccctacc cagcccagcc ctgccctgcc     480
ctgcccagct cagccctgcc caccccagcc cagcccagcc cagcatgcgt tctctggatg     540
gtgagcacag gcttgacctt agaaagaggc tggcaacgag ggctgaggcc accaggccac     600
tgggtgctca cgggtcagac aagcccagag cctgctcccc tgccacgggt cggggctgtc     660
accgccagca tgctgtggat gtgcatggcc tcagggctgc tggctccagg ctgccccgc      720 cctggctccc gaggccaccc ctcttatgcc atgaaccctg tgccacaccc acctctgagc     780
tgtccccgct cctgccgcct gcaccccctg agcagcccc tgtgtgtttc atgggagtct      840
tagcaaggaa ggggagctcg aattcctgca gcccggg                              877

<210> SEQ ID NO 21
<211> LENGTH: 1960
<212> TYPE: DNA
<213> ORGANISM: Artificial sequence
<220> FEATURE:
<223> OTHER INFORMATION: H19 downstream enhancer region
<220> FEATURE:
<221> NAME/KEY: misc_feature
<222> LOCATION: (1016)..(1016)
<223> OTHER INFORMATION: n is a, c, g, or t
<220> FEATURE:
<221> NAME/KEY: misc_feature
<222> LOCATION: (1126)..(1126)
<223> OTHER INFORMATION: n is a, c, g, or t

<400> SEQUENCE: 21
ccgggtaccg agctcccagg aagataaatg atttcctcct ctctagagat ggggtggga       60 tctgagcact cagagccaag ggcgcagtgg gtccgggcgg gggccctcct cggccctccc     120
aacatggggg ccaggaggtc agcccctcaa cctggacccc ggctgggtct cagggaatgg     180
tctcccccag tggcccagct tgcttgtgtt ttcagatggg tgtgcatggg tgtgtgtgtg     240
tgtgtgtgtg tgtgtgtgtg tgtgtgtgtg tgtgatgcct gacaagcccc agagagccaa     300
agacctgagt ggagatcttg tgacttctca aaaggggat tggaaggttc gagaaagagc      360
tgtggtcagc cttgctctcc cttaaggctg tggtaaccac actaggcata gcataggcct     420 gcgcccgtc cctccttccc tcctccgcgc ctctccttc tctttctccc ccctctaccc      480
cgctccctgg cctgctcctg gtgacaccgt tggccccctt ccaggctga gggaagccag      540 cggggccccc ttcctgaaag cccacctgca ggccggcttg ctgggaaggg gctgctctcg     600
cagaggctcc cgcccgccct gcagccgttt cctggaagca gtcgctgtgg gtattctgtt     660
ccttgtcagc actgtgcttg caaagaaagc agacactgtg ctccttgtcc ttagggagcc     720
ccgctccatc acccaacacc tggctggaca caggcgggag gccgggtccg cggggagcgg     780
cgcggggctg gggccggacc attaaacaca cacgggcgcc aggcactgca ggctcctcct     840
```

```
cctcctcctg cccagcgcct ctgctcacag gcacgtgcca agcccctagg ccaggaggcc      900
agcagtgggt gcagaacaag ctcctgggaa gggggtgcag ggcggacccc cggggagaag      960
ggctggcagg gctgtggggg acgctgaccg tgggccccac gttgcagaaa actggntgcc     1020
tggctggaag atgggggaga tgccaagcct ctgaggcagc acgagcaggg tgcatggagg     1080
ccggggcgcg gggaggctgc actgcagcat gcaccccaaa gcccanaggg agtgagacc      1140 aggccctgga atcgagaagt agaaaggcgg cttggaggcc tcggaaccgg ctgacctcca     1200
acagagtggg tctccagcct ggctctgccc tgccgcaggt cccctcccct cattaccagg     1260
cctagagcct ccagtcccgg tggcccccag cccgagggtg aacggcctca ccctgggtcg     1320
tgggacagag ggcacgttca tcaagagtgg ctcccaaggg acacgtggct gtttgcagtt     1380
cacaggaagc attcgagata aggagcttgt tttcccagtg ggcacggagc cagcaggggg     1440
gctgtggggc agcccagggt gcaaggccag gctgtggggc tgcagctgcc ttgggcccca     1500
ctcccaggcc tttgcgggag gtgggaggcg ggaggcggca gctgcacagt ggccccaggc     1560
gaggctctca gccccagtcg ctctccgggt gggcagccca agagggtctg gctgagcctc     1620
ccacatctgg gactccatca cccaacaact taattaaggc tgaatttcac gtgtcctgtg     1680
acttgggtag acaaagcccc tgtccaaagg ggcagccagc ctaaggcagt ggggacggcg     1740
tgggtggcgg gcgacggggg agatggacaa caggaccgag ggtgtgcggg cgatggggga     1800
gatggacaac aggaccgagg gtgtgcgggc gatgggggag atggacaaca ggaccgaggg     1860
tgtgcgggac acgcatgtca ctcatgcacg ccaatggggg gcgtgggagg ctggggagca     1920
gacagactgg gctgggctgg gcgggaagga cgggcagatg                           1960

<210> SEQ ID NO 22
<211> LENGTH: 4085
<212> TYPE: DNA
<213> ORGANISM: Artificial sequence
<220> FEATURE:
<223> OTHER INFORMATION: H19 downstream enhancer region
<220> FEATURE:
<221> NAME/KEY: misc_feature
<222> LOCATION: (1016)..(1016)
<223> OTHER INFORMATION: n is a, c, g, or t
<220> FEATURE:
<221> NAME/KEY: misc_feature
<222> LOCATION: (1126)..(1126)
<223> OTHER INFORMATION: n is a, c, g, or t
<220> FEATURE:
<221> NAME/KEY: misc_feature
<222> LOCATION: (2194)..(2194)
<223> OTHER INFORMATION: n is a, c, g, or t
<220> FEATURE:
<221> NAME/KEY: misc_feature
<222> LOCATION: (3235)..(3235)
<223> OTHER INFORMATION: n is a, c, g, or t

<400> SEQUENCE: 22
ccgggtaccg agctcccagg aagataaatg atttcctcct ctctagagat ggggtggga       60 tctgagcact cagagccaag ggcgcagtgg gtccgggcgg gggcccctcct cggccctccc    120 aacatggggg ccaggaggtc agcccctcaa cctggacccc ggctgggtct cagggaatgg     180
tctcccccag tggcccagct tgcttgtgtt ttcagatggg tgtgcatggg tgtgtgtgtg     240
tgtgtgtgtg tgtgtgtgtg tgtgtgtgtg tgtgatgcct gacaagcccc agagagccaa     300
agacctgagt ggagatcttg tgacttctca aaagggggat tggaaggttc gagaaagagc     360
tgtggtcagc cttgctctcc cttaaggctg tggtaaccac actaggcata gcataggcct     420
gcgccccgtc cctccttccc tcctccgcgc ctctccttc tctttctccc ccctctaccc     480
```

-continued

```
cgctccctgg cctgctcctg gtgacaccgt tggccccctt ccagggctga gggaagccag    540
cgggggcccc ttcctgaaag cccacctgca ggccggcttg ctgggaaggg gctgctctcg    600
cagaggctcc cgcccgccct gcagccgttt cctggaagca gtcgctgtgg gtattctgtt    660
ccttgtcagc actgtgcttg caaagaaagc agacactgtg ctccttgtcc ttagggagcc    720
ccgctccatc acccaacacc tggctggaca caggcgggag gccgggtccg cggggagcgg    780
cgcggggctg ggccggacc attaaacaca cacgggcgcc aggcactgca ggctcctcct    840
cctcctcctg cccagcgcct ctgctcacag gcacgtgcca agcccctagg ccaggaggcc    900
agcagtgggt gcagaacaag ctcctgggaa gggggtgcag ggcggacccc cggggagaag    960
ggctggcagg gctgtggggg acgctgaccg tgggccccac gttgcagaaa actggntgcc   1020
tggctggaag atgggggaga tgccaagcct ctgaggcagc acgagcaggg tgcatggagg   1080
ccggggcgcg ggaggctgc actgcagcat gcaccccaaa gcccanaggg agtggagacc    1140
aggccctgga atcgagaagt agaaaggcgg cttggaggcc tcggaaccgg ctgacctcca   1200
acagagtggg gccggccctg gaggcaaaga ggtgcccggg gtccggccct gcctggggga   1260
gctatgtgtc atgggcaagc acaggatat gtagcccgct ctgagcctat ggacccaggg    1320
cagggctgca aggcagggca ggggagacag cacgggggag caaggagcag agagggggcc   1380
tcaggctctc ccaggaggaa cattctcccg acaggaggaa gagacggccc aggggtgact   1440
gtggggagcc atggtggcag ctgggtcgt ggcagatggg agagaggctg gcgaggtgaa    1500
ggtgcagggg tcagggctct ggggcccaca tgcctgtggg agcaggcagg cccagggctc   1560
tccgccactc cccactcccg cttggctcat aggctgggcc caagggtggg gtgggatgag   1620
caggagatgg ggcccagggg gcaagcaggg ccccaaagac atttagaaaa accggtttat   1680
gcaggcagca ttcagagcag gcggcgtgcg tggcggggc cctgggagca cagagaggca    1740
cacgtagggc ccccgagggg ctccccattg gccggcagtg acatcacccc tgtgtcaaca   1800
gtgatgtctg cagctccggc cagccagggt ttatggagcg agacccagcc cggcctgggc   1860
cctcactccc caggcccaca cactagccca ctgttcaggg tccggggtgg cggcatggcc   1920
tgggggtcct ggcaccgctg ctcctctgcc caccctaact tccggcatc gcggctgccc    1980 cctctgagcg tccccaacca gtaagtgtgg ggcccagcag gcctgccgtc ctcctcctct   2040
tcccctctag agagaaacgt ggaggtcctg gggctggggg cgctcatagc cctgtgacac   2100
aggtgcatgg ggtcagggt cccagaatgg cccctgggaa ggacctcagc tgggccggcg    2160
gctctaggct tcagggtct gtctgcacag gggntagccc ctcccagacc tctgtgaagc    2220
cagtacgggc ctcccctccc tgccccgtgc tctgtccggt gcttcctgga ctgcactgcg   2280
ggccactggt gagagggtgg acaggaagg gccgccgtgg tgcctgttcc tgcccacctg    2340
gctgtgtggt cccctccaag tagggacaac ccttctgagg gcttgggggc acctggggt    2400 tgccagggcc tcccagagcc ctgtgagccc ctgggggtc tggcctgatg ccccctcca    2460 cgtccagggc cggctgtggc ccagaacccc agcttccag caggccggtg tgcggtggtg    2520
acccaggaga ggcctcgcct ccactgaggg gccaccgacc tctgtcagac cacagagacc   2580
cccaaggagt ctgaaggctg gagacccggg gctgggacca ggtgggactt tcccacggag   2640
ccgtccccag gcccagctgg ggacacgtcc cccttctctc cagacacacc ctgcctgcca   2700
ccaggacaca ccggcctgtt gggggtctct tttaagtgct tgccactctg aggtgactgt   2760
ccctttccaa agaggtttct ggggcccagg tgggatgcgt cggcctgagc aggaggatct   2820
gggccgccag gggctgggga ctgtctcctg gggaaggaag cgcctgggag cgtgtgtgct   2880
```

```
gacccaggac catccaggga ggcccgtctg tggggcaagc gggaagggag cggctggaga    2940
ggcttggccg cccccgccct gcctcccatt ccttagctcc atgcctgtca acctctgtca    3000
cccagtgagt gatgtccagg ggccctggaa aggtcacagc atgtttgagc ggggtgagag    3060
agagggaaa ggcgggggcg gggaaaagta cgtggaggaa gctttaggcc caaggaagga    3120
gacagggttc tgggagggag ggagccactg gggccgccgg gaaggtccct gcttgctgct    3180
gccacccaga accctcgcct cttagctagc ccccgcagcc ccagcctttc tggcntgtgg    3240
ccctctcccc catccccagg tgtcctgtgc aaccaggcct tggacccaaa ccctcctgcc    3300
ccctcctctc cctcctcacc ctcccaatgc agtggtctcc agcctggctc tgccctgccg    3360
caggtcccct cccctcatta ccaggcctag agcctccagt cccggtggcc cccagcccga    3420
gggtgaacgg cctcaccctg ggtcgtggga cagagggcac gttcatcaag agtggctccc    3480
aagggacacg tggctgtttg cagttcacag gaagcattcg agataaggag cttgttttcc    3540
cagtgggcac ggagccagca gggggggctgt ggggcagccc agggtgcaag gccaggctgt    3600
ggggctgcag ctgccttggg ccccactccc aggcctttgc gggaggtggg aggcgggagg    3660
cggcagctgc acagtggccc caggcgaggc tctcagcccc agtcgctctc cgggtgggca    3720
gcccaagagg gtctggctga gcctcccaca tctgggactc catcacccaa caacttaatt    3780
aaggctgaat ttcacgtgtc ctgtgacttg ggtagacaaa gcccctgtcc aaaggggcag    3840
ccagcctaag gcagtgggga cggcgtgggt ggcgggcgac gggggagatg gacaacagga    3900
ccgagggtgt gcgggcgatg ggggagatgg acaacaggac cgagggtgtg cgggcgatgg    3960
gggagatgga caacaggacc gagggtgtgc gggacacgca tgtcactcat gcacgccaat    4020
gggggggcgtg ggaggctggg gagcagacag actgggctgg gctgggcggg aaggacgggc    4080
agatg                                                                4085
```